United States Patent [19]

Maeda et al.

[11] Patent Number: 5,194,586

[45] Date of Patent: Mar. 16, 1993

[54] ANTI-ATLA ANTIBODY BINDING PEPTIDES

[75] Inventors: Yoshiaki Maeda, Fukuoka; Hiroshi Shiraki, Onojo; Yukiko Washitani, Fukuoka; Naotaka Kuroda, Onojo; Kyoko Yamada, Kurashiki; Kiichiro Oka, Kurashiki; Toshihiko Namba, Kurashiki, all of Japan

[73] Assignee: Kuraray Co., Ltd., Okayama, Japan

[21] Appl. No.: 596,081

[22] Filed: Oct. 11, 1990

[30] Foreign Application Priority Data

Oct. 13, 1989 [JP] Japan ................. 1-266983

[51] Int. Cl.$^5$ ................. A61K 37/02; C07K 5/00; C07K 7/00; C12Q 1/00
[52] U.S. Cl. .................... 530/324; 530/325; 530/326
[58] Field of Search ............. 530/324, 325, 326; 435/7; 514/12

[56] References Cited

U.S. PATENT DOCUMENTS 3,907,755 9/1975 Margraff et al. ............ 525/420
4,629,783 12/1986 Cosand ................. 530/324

FOREIGN PATENT DOCUMENTS 0107053 5/1984 European Pat. Off. .
8601834 3/1986 PCT Int'l Appl. .
8805783 8/1988 PCT Int'l Appl. .

OTHER PUBLICATIONS

Hattori et al., Virology, 136, pp. 338-347, 1984.
JP 60 28,993, Otsuka Pharmaceuticals, Chemical Abstracts, vol. 104, p. 801, 1986, Ab No. 207681j.
Zavyalov et al., Immunology Letters, vol. 14, pp. 139-142, (1986/1987).

Primary Examiner—Merrell C. Cashion, Jr.
Assistant Examiner—A. M. Davenport

[57] ABSTRACT

A peptide of the general formula:

H-X-A-Y wherein A is a peptide fragment comprising 6 to 50 amino acids, X is a peptide fragment comprising 1 to 10 Lys, and Y is hydroxy or amino group, said peptide being capable of specifically binding to an antibody having a specificity against an adult T cell leukemia associated antigen, a reagent for measuring an antibody having a specificity against an adult T cell leukemia associated antigen which comprises the peptide, and an adsorbent for an antibody having a specificity against an adult T cell leukemia associated antigen which comprises the peptide immobilized on a carrier.

4 Claims, 6 Drawing Sheets

SEQUENCE LISTING ( 1 ) GENERAL INFORMATION:

( i i i ) NUMBER OF SEQUENCES: 40

( 2 ) INFORMATION FOR SEQ ID NO:1:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:1:

Pro Pro Pro Pro Ser Ser Pro Thr His Asp Pro Pro Asp Ser Asp Pro

```
                    1                 5                        10                        15
            Gln  Ile  Pro  Pro  Pro  Tyr  Val  Glu  Pro  Thr  Ala  Pro  Gln  Val  Leu
                              20                 25                       30
```

( 2 ) INFORMATION FOR SEQ ID NO:2:

( i ) SEQUENCE CHARACTERISTICS:
       ( A ) LENGTH: 19 amino acids
       ( B ) TYPE: amino acid
       ( D ) TOPOLOGY: linear ( i i ) MOLECULE TYPE: peptide ( v ) FRAGMENT TYPE: internal ( x i ) SEQUENCE DESCRIPTION: SEQ ID NO:2:

```
            Tyr  Ala  Ala  Gln  Asn  Arg  Arg  Gly  Leu  Asp  Leu  Leu  Phe  Trp  Glu  Gln
            1                 5                         10                        15

Gly  Gly  Leu
```

( 2 ) INFORMATION FOR SEQ ID NO:3:

( i ) SEQUENCE CHARACTERISTICS:
       ( A ) LENGTH: 25 amino acids
       ( B ) TYPE: amino acid
       ( D ) TOPOLOGY: linear ( i i ) MOLECULE TYPE: peptide ( v ) FRAGMENT TYPE: internal ( x i ) SEQUENCE DESCRIPTION: SEQ ID NO:3:

```
            Phe  Leu  Asn  Thr  Glu  Pro  Ser  Gln  Leu  Pro  Pro  Thr  Ala  Pro  Pro  Leu
            1                 5                         10                        15

Leu  Pro  His  Ser  Asn  Leu  Asp  His  Ile
                              20                 25
```

( 2 ) INFORMATION FOR SEQ ID NO:4:

( i ) SEQUENCE CHARACTERISTICS:
       ( A ) LENGTH: 4 amino acids
       ( B ) TYPE: amino acid
       ( D ) TOPOLOGY: linear ( i i ) MOLECULE TYPE: peptide ( v ) FRAGMENT TYPE: N-terminal ( x i ) SEQUENCE DESCRIPTION: SEQ ID NO:4:

```
            Lys  Lys  Lys  Lys
            1
```

( 2 ) INFORMATION FOR SEQ ID NO:5:

( i ) SEQUENCE CHARACTERISTICS:
       ( A ) LENGTH: 5 amino acids
       ( B ) TYPE: amino acid
       ( D ) TOPOLOGY: linear ( i i ) MOLECULE TYPE: peptide ( v ) FRAGMENT TYPE: N-terminal ( x i ) SEQUENCE DESCRIPTION: SEQ ID NO:5:

```
            Lys  Lys  Lys  Lys  Lys
            1                 5
```

( 2 ) INFORMATION FOR SEQ ID NO:6:

( i ) SEQUENCE CHARACTERISTICS:
       ( A ) LENGTH: 33 amino acids
       ( B ) TYPE: amino acid (D) TOPOLOGY: linear (i i) MOLECULE TYPE: peptide (x i) SEQUENCE DESCRIPTION: SEQ ID NO:6:

```
Lys Lys Pro Pro Pro Pro Ser Ser Pro Thr His Asp Pro Pro Asp Ser
1               5                   10                  15
Asp Pro Gln Ile Pro Pro Pro Tyr Val Glu Pro Thr Ala Pro Gln Val
            20              25                  30
Leu
```

(2) INFORMATION FOR SEQ ID NO:7:

(i) SEQUENCE CHARACTERISTICS:
        (A) LENGTH: 22 amino acids
        (B) TYPE: amino acid
        (D) TOPOLOGY: linear (i i) MOLECULE TYPE: peptide (x i) SEQUENCE DESCRIPTION: SEQ ID NO:7:

```
Lys Lys Lys Pro Pro Pro Pro Ser Ser Pro Thr His Asp Pro Pro Asp
1               5                   10                  15
Ser Asp Pro Gln Ile Pro
            20
```

(2) INFORMATION FOR SEQ ID NO:8:

(i) SEQUENCE CHARACTERISTICS:
        (A) LENGTH: 16 amino acids
        (B) TYPE: amino acid
        (D) TOPOLOGY: linear (i i) MOLECULE TYPE: peptide (x i) SEQUENCE DESCRIPTION: SEQ ID NO:8:

```
Lys Lys Lys Lys Lys Pro Tyr Val Glu Pro Thr Ala Pro Gln Val Leu
1               5                   10                  15
```

(2) INFORMATION FOR SEQ ID NO:9:

(i) SEQUENCE CHARACTERISTICS:
        (A) LENGTH: 33 amino acids
        (B) TYPE: amino acid
        (D) TOPOLOGY: linear (i i) MOLECULE TYPE: peptide (x i) SEQUENCE DESCRIPTION: SEQ ID NO:9:

```
Lys Lys Lys Pro Val Met His Pro His Gly Ala Pro Pro Asn His Arg
1               5                   10                  15
Pro Trp Gln Met Lys Asp Leu Gln Ala Ile Lys Gln Glu Val Ser Gln
            20              25                  30
Ala
```

(2) INFORMATION FOR SEQ ID NO:10:

(i) SEQUENCE CHARACTERISTICS:
        (A) LENGTH: 32 amino acids
        (B) TYPE: amino acid
        (D) TOPOLOGY: linear (i i) MOLECULE TYPE: peptide (x i) SEQUENCE DESCRIPTION: SEQ ID NO:10:

```
Lys Lys Gly Leu Pro Glu Gly Thr Pro Lys Asp Pro Ile Leu Arg Ser
1               5                   10                  15
```

```
    Leu  Ala  Tyr  Ser  Asn  Ala  Asn  Lys  Glu  Cys  Gln  Lys  Leu  Leu  Gln  Ala
              20                       25                       30
```

(2) INFORMATION FOR SEQ ID NO:11:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:11:

```
  Lys  Lys  Lys  Lys  Lys  Asp  Pro  Ile  Leu  Arg  Ser  Leu  Ala  Tyr  Ser  Asn
  1                   5                        10                       15

Ala  Asn  Lys  Glu  Cys  Gln  Lys  Leu
                  20
```

(2) INFORMATION FOR SEQ ID NO:12:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:12:

```
  Lys  Lys  Gly  Asp  Tyr  Ser  Pro  Ser  Cys  Cys  Thr  Leu  Thr  Ile  Gly  Val
  1                   5                        10                       15

Ser  Ser  Tyr  His  Ser  Lys  Pro  Cys  Asn  Pro  Ala  Gln  Pro  Val  Cys  Ser
                  20                       25                       30
```

(2) INFORMATION FOR SEQ ID NO:13:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO:13:

```
  Lys  Lys  Lys  Thr  Lys  Lys  Pro  Asn  Arg  Asn  Gly  Gly  Gly  Tyr  Tyr  Ser
  1                   5                        10                       15

Ala  Ser  Tyr  Ser  Asp  Pro  Cys  Ser  Leu  Lys  Cys  Pro  Tyr  Leu
                  20                       25                       30
```

(2) INFORMATION FOR SEQ ID NO:14:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:14:

```
  Lys  Lys  Lys  Phe  Leu  Asn  Thr  Glu  Pro  Ser  Gln  Leu  Pro  Pro  Thr  Ala
  1                   5                        10                       15

Pro  Pro  Leu  Leu  Pro  His  Ser  Asn  Leu  Asp  His  Ile
                  20                       25
```

(2) INFORMATION FOR SEQ ID NO:15:

(i) SEQUENCE CHARACTERISTICS:
        (A) LENGTH: 34 amino acids
        (B) TYPE: amino acid
        (D) TOPOLOGY: linear ( i i ) MOLECULE TYPE: peptide ( x i ) SEQUENCE DESCRIPTION: SEQ ID NO:15:

Lys Lys Lys Lys Thr Pro Leu Leu Tyr Pro Ser Leu Ala Leu Pro Ala
1               5                   10                  15

Pro His Leu Thr Leu Pro Phe Asn Trp Thr His Cys Phe Asp Pro Gln
                20                  25                  30

Ile Gln ( 2 ) INFORMATION FOR SEQ ID NO:16:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

Lys Lys Thr Pro Cys His Asn Ser Leu Ile Leu Pro Pro Phe Ser Leu
1               5                   10                  15

Ser Pro Val Pro Thr Leu Gly Ser Arg Ser Arg Arg Ala Val Pro Val
                20                  25                  30

Ala ( 2 ) INFORMATION FOR SEQ ID NO:17:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

Lys Lys Lys Val Asp Lys Asp Ile Ser Gln Leu Thr Gln Ala Ile Val
1               5                   10                  15

Lys Asn His Lys Asn Leu Leu Lys Ile Ala Gln Tyr Ala Ala Gln Asn
                20                  25                  30

Arg Arg Gly Leu Asp Leu Leu Phe
            35                  40

( 2 ) INFORMATION FOR SEQ ID NO:18:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

Lys Lys Cys Arg Phe Pro Asn Ile Thr Asn Ser His Val Pro Ile Leu
1               5                   10                  15

Gln Glu Arg Pro Pro Leu Glu Asn Arg Val Leu Thr Gly Trp Gly Leu
                20                  25                  30

( 2 ) INFORMATION FOR SEQ ID NO:19:

( i ) SEQUENCE CHARACTERISTICS:
        ( A ) LENGTH: 34 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:19:

Lys Lys Lys Leu Ala Gly Pro Cys Ile Leu Arg Gln Leu Arg His Leu
1               5                   10                  15

Pro Ser Arg Val Arg Tyr Pro His Tyr Ser Leu Ile Lys Pro Glu Ser
            20                  25                  30

Ser Leu ( 2 ) INFORMATION FOR SEQ ID NO:20:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:20:

Lys Lys Tyr Ala Ala Gln Asn Arg Arg Gly Leu Asp Leu Leu Phe Trp
1               5                   10                  15

Glu Gln Gly Gly Leu
            20

( 2 ) INFORMATION FOR SEQ ID NO:21:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:21:

Lys Lys Leu Leu Pro His Ser Asn Leu Asp His Ile Leu Glu Pro Ser
1               5                   10                  15

Ile Pro Trp Lys Ser Lys
            20

( 2 ) INFORMATION FOR SEQ ID NO:22:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

Lys Lys Lys Lys Tyr Ala Ala Gln Asn Arg Arg Gly Leu Asp Leu Leu
1               5                   10                  15

Phe Trp Glu Gln Gly Gly Leu
            20

( 2 ) INFORMATION FOR SEQ ID NO:23:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:

Lys Lys Lys Lys Lys Tyr Ala Ala Gln Asn Arg Arg Gly Leu Asp Leu
1               5                   10                  15

Leu Phe Trp Glu Gln Gly Gly Leu
            20

( 2 ) INFORMATION FOR SEQ ID NO:24:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:24:

```
Pro  Pro  Pro  Pro  Ser  Ser  Pro  Thr  His  Asp  Pro  Pro  Asp  Ser  Asp  Pro
1                   5                        10                       15

Gln  Ile  Pro  Pro  Pro  Tyr  Val  Glu  Pro  Thr  Ala  Pro  Gln  Val  Leu
              20                      25                       30
```

( 2 ) INFORMATION FOR SEQ ID NO:25:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:25:

```
Leu  Leu  Pro  His  Ser  Asn  Leu  Asp  His  Ile  Leu  Glu  Pro  Ser  Ile  Pro
1                   5                        10                       15

Trp  Lys  Ser  Lys
              20
```

( 2 ) INFORMATION FOR SEQ ID NO:26:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:26:

```
Tyr  Ala  Ala  Gln  Asn  Arg  Arg  Gly  Leu  Asp  Leu  Leu  Phe  Trp  Glu  Gln
1                   5                        10                       15

Gly  Gly  Leu
```

( 2 ) INFORMATION FOR SEQ ID NO:27:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:27:

```
Phe  Leu  Asn  Thr  Glu  Pro  Ser  Gln  Leu  Pro  Pro  Thr  Ala  Pro  Pro  Leu
1                   5                        10                       15

Leu  Pro  His  Ser  Asn  Leu  Asp  His  Ile
              20                      25
```

( 2 ) INFORMATION FOR SEQ ID NO:28:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:28:

```
    Pro Pro Pro Pro Ser Ser Pro Thr His Asp Pro Pro Asp Ser Asp Pro
    1               5                   10                  15

Gln Ile Pro
```

(2) INFORMATION FOR SEQ ID NO:29:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:29:

```
    Pro Tyr Val Glu Pro Thr Ala Pro Gln Val Leu
    1               5                   10
```

(2) INFORMATION FOR SEQ ID NO:30:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO:30:

```
    Pro Val Met His Pro His Gly Ala Pro Pro Asn His Arg Pro Trp Gln
    1               5                   10                  15

Met Lys Asp Leu Gln Ala Ile Lys Gln Glu Val Ser Gln Ala
                    20                  25                  30
```

(2) INFORMATION FOR SEQ ID NO:31:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO:31:

```
    Gly Leu Pro Glu Gly Thr Pro Lys Asp Pro Ile Leu Arg Ser Leu Ala
    1               5                   10                  15

Tyr Ser Asn Ala Asn Lys Glu Cys Gln Lys Leu Leu Gln Ala
                    20                  25                  30
```

(2) INFORMATION FOR SEQ ID NO:32:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (xi) SEQUENCE DESCRIPTION: SEQ ID NO:32:

```
    Asp Pro Ile Leu Arg Ser Leu Ala Tyr Ser Asn Ala Asn Lys Glu Cys
    1               5                   10                  15

Gln Lys Leu
```

(2) INFORMATION FOR SEQ ID NO:33:

(i) SEQUENCE CHARACTERISTICS:
        (A) LENGTH: 30 amino acids
        (B) TYPE: amino acid
        (D) TOPOLOGY: linear ( i i ) MOLECULE TYPE: peptide ( x i ) SEQUENCE DESCRIPTION: SEQ ID NO:33:

Gly Asp Tyr Ser Pro Ser Cys Cys Thr Leu Thr Ile Gly Val Ser Ser
1               5                   10                  15

Tyr His Ser Lys Pro Cys Asn Pro Ala Gln Pro Val Cys Ser
                20                  25                  30

( 2 ) INFORMATION FOR SEQ ID NO:34:

( i ) SEQUENCE CHARACTERISTICS:
    ( A ) LENGTH: 27 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:34:

Thr Lys Lys Pro Asn Arg Asn Gly Gly Gly Tyr Tyr Ser Ala Ser Tyr
1               5                   10                  15

Ser Asp Pro Cys Ser Leu Lys Cys Pro Tyr Leu
                20                  25

( 2 ) INFORMATION FOR SEQ ID NO:35:

( i ) SEQUENCE CHARACTERISTICS:
    ( A ) LENGTH: 30 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:35:

Thr Pro Leu Leu Tyr Pro Ser Leu Ala Leu Pro Ala Pro His Leu Thr
1               5                   10                  15

Leu Pro Phe Asn Trp Thr His Cys Phe Asp Pro Gln Ile Gln
                20                  25                  30

( 2 ) INFORMATION FOR SEQ ID NO:36:

( i ) SEQUENCE CHARACTERISTICS:
    ( A ) LENGTH: 31 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:36:

Thr Pro Cys His Asn Ser Leu Ile Leu Pro Pro Phe Ser Leu Ser Pro
1               5                   10                  15

Val Pro Thr Leu Gly Ser Arg Ser Arg Arg Ala Val Pro Val Ala
                20                  25                  30

( 2 ) INFORMATION FOR SEQ ID NO:37:

( i ) SEQUENCE CHARACTERISTICS:
    ( A ) LENGTH: 37 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:37:

Val Asp Lys Asp Ile Ser Gln Leu Thr Gln Ala Ile Val Lys Asn His
1               5                   10                  15

Lys Asn Leu Leu Lys Ile Ala Gln Tyr Ala Ala Gln Asn Arg Arg Gly
                20                  25                  30

```
Leu Asp Leu Leu Phe
            35
```

( 2 ) INFORMATION FOR SEQ ID NO:38:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:38:

```
Cys Arg Phe Pro Asn Ile Thr Asn Ser His Val Pro Ile Leu Gln Glu
 1           5                   10                   15
Arg Pro Pro Leu Glu Asn Arg Val Leu Thr Gly Trp Gly Leu
            20                  25                  30
```

( 2 ) INFORMATION FOR SEQ ID NO:39:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:39:

```
Leu Ala Gly Pro Cys Ile Leu Arg Gln Leu Arg His Leu Pro Ser Arg
 1           5                   10                  15
Val Arg Tyr Pro His Tyr Ser Leu Ile Lys Pro Glu Ser Ser Leu
            20                  25                  30
```

( 2 ) INFORMATION FOR SEQ ID NO:40:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:40:

```
Leu Leu Pro His Ser Asn Leu Asp His Ile Leu Glu Pro Ser Ile Pro
 1           5                   10                  15
Trp Lys Ser Lys
            20
```

ANTI-ATLA ANTIBODY BINDING PEPTIDES

The present invention relates to a peptide and use thereof. The peptide of the present invention is novel and is capable of specifically binding to an antibody having a specificity against an adult T cell leukemia associated antigen (hereinafter referred to as "ATLA"), said antibody being hereinafter referred to as "anti-ATLA antibody". The peptide of the present invention can be used for measuring an anti-ATLA antibody, for purification of an anti-ATLA antibody, and as an adsorbent for removing the anti-ATLA antibody from the body of an adult T cell leukemia virus carrier.

A reagent for measuring the anti-ATLA antibody and an adsorbent for the anti-ATLA antibody of the present invention have an ability to detect the anti-ATLA antibody in serum or plasma with high sensitivity and an ability to adsorb the anti-ATLA antibody in serum or plasma with high specificity, and hence, are useful for measurement and purification of the anti-ATLA antibody and for treatment of an adult T cell leukemia virus-infectious disease.

TECHNICAL BACKGROUND AND PRIOR ART

It is known that an adult T cell leukemia virus (hereinafter referred to as "ATLV"), which has been isolated from patients with adult T cell leukemia (hereinafter referred to as "ATL"), infects immunocompetent cells and causes a variety of immunological disorders or decrease of immunological competence including ATL [cf. Proceedings of the National Academy of Science of the United States of America, 78, 6476 (1981)]. The nucleotide sequence of the gene of said virus is known [cf. Proceedings of the National Academy of Science of the United States of America, 80, 3618 (1983)]. For detection of the anti-ATLA antibody or preparation of vaccine for prophylaxis or treatment of ATL, a recombinant protein of ATLV-related antigen has been prepared by the gene engineering technique [cf. Japanese Patent Application Laid-open KOKAI No. 124963/1988; Gene, 38, 57 (1985); Proceedings of the National Academy of Science of the United States of America, 81, 6202 (1984)] or a synthetic peptide of ATLV-related antigen has been prepared by the peptide synthesis technique [cf. Journal of Immunology, 136, No. 7, 2393 (1986); Virology, 136, 338 (1984); Japanese Patent Application Laid-open KOKAI No. 301896/1988; Japanese Patent Application Laid-open KOKAI No. 30600/1986; Leukemia Research, 9, No. 9, 1111 (1985)].

Diseases caused by ATLV include those directly caused by ATLV such as ATL and HTLV-I associated myelopathy, and those indirectly caused by ATLV such as chronic pulmonary diseases, opportunistic pulmonary infections, M proteinosis, chronic renal failure, immunodeficiency (e.g. non-specific dermatomycosis, etc.), and the like. At present, ATL has been treated mainly by symptomatic therapy for those diseases having no subjective symptoms or for chronically progressing diseases or by chemotherapy using multiple drugs, especially anti-tumor agents, for progressive ATL. However, the effects of these methods are not clear, and hence, more improved method is desired for treating the above mentioned diseases more effectively and surely.

At present, the anti-ATLA antibody has been detected by an indirect immunofluorescence method in which ATLV-infected cells are coated onto a slide glass and the anti-ATLA antibody is detected using an antibody labelled with fluorochrome [Nature, 294, 770 (1981)], by a particle agglutination method utilizing the phenomenon that gelatin particles sensitized with ATLV or antigenic components thereof agglutinate in the presence of the anti-ATLA antibody [Gann, 7, 845 (1984)], by a radioimmunoassay using a microcup coated with antigenic components extracted from ATLV-infected cells [Journal of Experimental Medicine, 159, 1117 (1984)] or by an enzyme-linked immunosorbent assay (hereinafter referred to as "ELISA") [Gann, 74, 185 (1983)].

However, ATLV-infected cells and partially purified antigenic components obtained therefrom also contain various non-specific antigenic components. Therefore, when the anti-ATLA antibody is measured using these ATLV-infected cells or antigenic components thereof as a reagent, these reagents are also recognized by another non-specific antibodies in a specimen other than the target anti-ATLA antibody such as an anti-nuclear antibody and an anti-T cell antibody. As a result, the presence of the anti-ATLA antibody is not correctly determined by these methods.

For overcoming this problem, many studies have been made as to radioimmunoassay or ELISA using a recombinant protein or synthetic peptide. For example, methods using the recombinant protein include those using an env protein which is considered to have a high antigenicity [Science, 226, 1094 (1984); Proceedings of the National Academy of Science of the United States of America, 81, 6202 (1984); Japanese Patent Application Laid-open KOKAI No. 166624/1985; Japanese Patent Application Laid-open KOKAI No. 166699/1985], those using a gag protein [Gene, 38, 57 (1985); Japanese Patent Application Laid-open KOKAI No. 61534/1985; Japanese Patent Application Laid-open KOKAI No. 124963/1988] and the like. As the methods using synthetic peptide, there have been reported a radioimmunoassay using peptides corresponding to amino acid sequences of hydrophilic regions selected from the gag protein region or env protein region of ATLV, said peptides being synthesized by peptide synthesizer [Journal of Immunology, 136, No. 7, 2393 (1986); Journal of Immunology, 142, No. 3, 971 (1989); Proceedings of the National Academy of Science of the United States of America, 84, 2479 (1987)] and the like. Although these methods utilize the recombinant proteins or synthetic peptides which do not contain non-specific components, they are disadvantageous in that the recombinant proteins or synthetic peptides in these methods show only low specificity against the anti-ATLA antibody and that they are not safe due to the use of radioactive substances. Therefore, it has been desired to develop a method for measuring the anti-ATLA antibody which does not involve the use of radioactive substances and utilizes an antigenic polypeptide which is highly specific against the anti-ATLA antibody.

BRIEF SUMMARY OF THE INVENTION

An object of the present invention is to provide a peptide capable of specifically binding to the anti-ATLA antibody.

Another object of the present invention is to provide a reagent for measuring the anti-ATLA antibody.

Further object of the present invention is to provide an adsorbent capable of absorbing the anti-ATLA antibody.

These and other objects and advantages of the invention will be apparent to those skilled in the art from the following description.

BRIEF DESCRIPTION OF THE DRAWINGS

In FIGS. 1a and 1b, each mark represents as follows:

● : $OD_{492}$ values obtained from the ATLV-carrier serum;

○ : $OD_{492}$ values obtained from the normal human serum.

FIGS. 2a, 2b, 2c, 2d, 2e, 2f and 2g are graphs showing the $OD_{492}$ values obtained by the method described in Example 20 using various coating amounts of the peptide prepared in Example 1 and the peptide prepared in Reference Example 1 for each serum specimen No. 1 to No. 7, respectively. In FIGS. 2a, 2b, 2c, 2d, 2e, 2f and 2g, each mark represents as follows:

-●- : $OD_{492}$ values obtained by using the peptide prepared in Example 1 for each serum specimen;

-○- : $OD_{492}$ values obtained by using the peptide prepared in Reference Example 1 for each serum specimen.

Figure 3A:
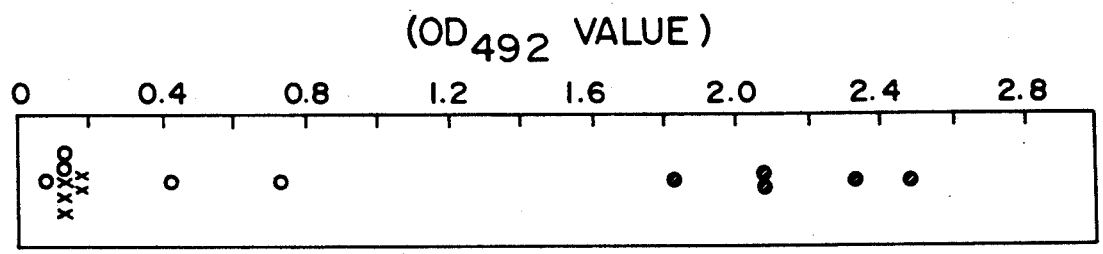
Figure 3B:
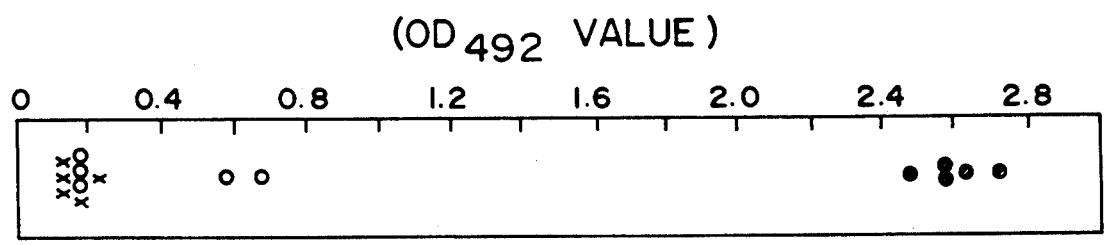
Figure 3C:
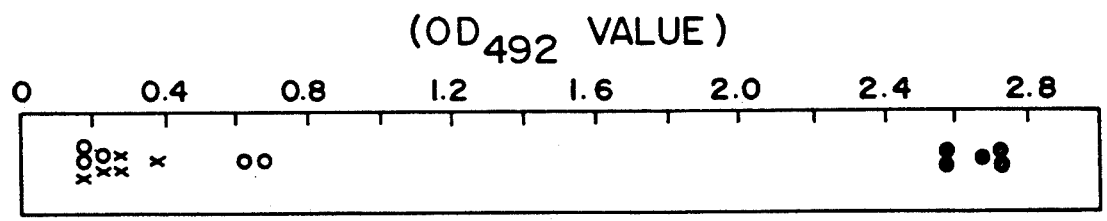

FIGS. 3a, 3b and 3c are graphs showing the distribution of the $OD_{492}$ values obtained by the method described in Example 21 using the three kind of assay cups coated with the peptide prepared in Example 1 for each serum specimen. In FIGS. 3a, 3b and 3c, each mark represents as follows:

● : $OD_{492}$ values obtained from ATLV-carrier serum;

○ : $OD_{492}$ values obtained from ATLV-false-positive serum;

x : $OD_{492}$ values obtained from normal human serum.

Figure 4A:
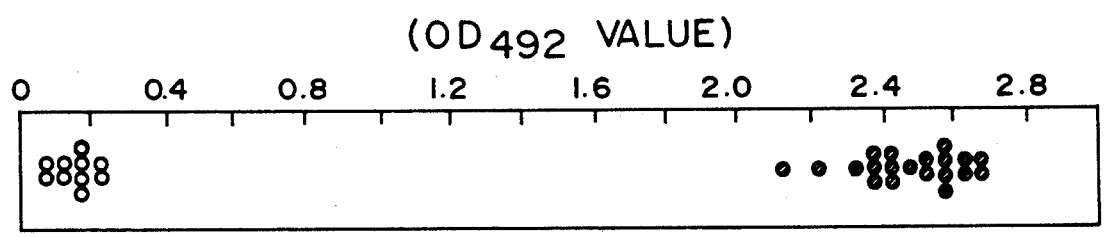
Figure 4B:
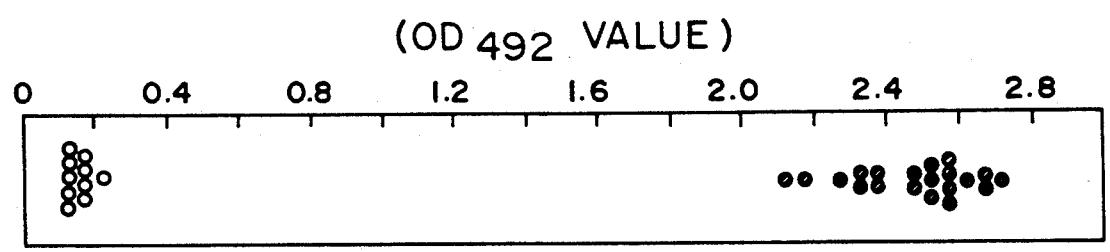

FIGS. 4a and 4b are graphs showing the distribution of the $OD_{492}$ values obtained by the method described in Example 22 using the peptide prepared in Example 15 and the peptide prepared in Example 16 for each serum specimen. In FIGS. 4a and 4b, each mark represents as follows:

● : $OD_{492}$ values obtained from ATLV-carrier serum;

○ : $OD_{492}$ values obtained from normal human serum.

DETAILED DESCRIPTION OF THE INVENTION

According to the present invention, there are provided a peptide of the general formula:

$$H-X-A-Y \quad (I)$$

wherein A is a peptide fragment comprising 6 to 50 amino acids, X is a peptide fragment comprising 1 to 10 Lys, and Y is hydroxyl or amino group, said peptide being capable of specifically binding to an antibody having a specificity against an adult T cell leukemia associated antigen (hereinafter referred to as "peptide (I)"); a reagent for measuring the anti-ATLA antibody which comprises the peptide (I); and an adsorbent for the anti-ATLA antibody which comprises the peptide (I) immobilized on a carrier.

In the specification, each amino acid residue is abbreviated as follows:
Ala: L-alanine residue
Arg: L-arginine residue
Asn: L-asparagine residue
Asp L-aspartic acid residue
Cys: L-cysteine residue
Gln: L-glutamine residue
Glu: L-glutamic acid residue
Gly: Glycine residue
His: L-histidine residue
Ile: L-isoleucine residue
Leu: L-leucine residue
Lys: L-lysine residue
Met: L-methionine residue
Phe: L-phenylalanine residue
Pro: L-proline residue
Ser: L-serine residue
Thr: L-threonine residue
Trp: L-tryptophan residue
Tyr: L-tyrosine residue
Val: L-valine residue Also in the specification, the amino acid sequence is described in such a way that the amino acid residue at the N-terminus of the sequence is on the left hand and the amino acid residue at the C-terminus of the sequence is on the right hand in the usual manner.

The peptide fragment for A in the formula (I) is preferably peptide fragments comprising 6 to 50 amino acids derived from the antigenic polypeptide coded by an ATLV gene. Among these, particularly preferable are a peptide fragment coded by the gag gene having the following amino acid sequence (A-1) which is identified in the Sequence Listing as SEQ ID NO: 1 :

—Pro—Pro—Pro—Pro—Ser—Ser—Pro—Thr—His—Asp— (A-1)

Pro—Pro—Asp—Ser—Asp—Pro—Gln—Ile—Pro—Pro—

Pro—Tyr—Val—Glu—Pro—Thr—Ala—Pro—Gln—Val—

Leu—, and peptide fragments coded by the env gene having the following amino acid sequences (A-2) and (A-3) which are identified in the Sequence Listing respectively as SEQ ID NO: 2 and SEQ ID NO: 3:

—Tyr—Ala—Ala—Gln—Asn—Arg—Arg—Gly—Leu—Asp— (A-2)

Leu—Leu—Phe—Trp—Glu—Gln—Gly—Gly—Leu—, and

—Phe—Leu—Asn—Thr—Glu—Pro—Ser—Gln—Leu—Pro— (A-3)

Pro—Thr—Ala—Pro—Pro—Leu—Leu—Pro—His—Ser—

Ans—Leu—Asp—His—Ile—.

A peptide fragment comprising five or less amino acids does not show specific antigenicity against the anti-ATLA antibody. It is difficult to synthesize a peptide fragment comprising fifty one or more amino acids having the desired specific antigenicity against the anti-ATLA antibody.

As the peptide fragment for X in the formula (I), a peptide fragment of the formula: -Lys-Lys-, a peptide fragment of the formula: -Lys-Lys-Lys-, and the like are preferable. When the peptide fragment of X comprises eleven or more Lys residues, the peptide of the formula (I) tends not to have specific antigenicity against the anti-ATLA antibody. In case that the peptide fragment of X contains an amino acid residue other than Lys, the peptide of the formula (I) tends not to be capable of specifically binding to the anti-ATLA antibody or not to be capable of being coated or immobilized on the carrier efficiently.

The peptide (I) is synthesized by the method usually used for the peptide synthesis, including a solid phase technique or a liquid phase technique (e.g stepwise elongation method, fragment fusion method, etc.). The solid phase technique is preferable from the viewpoint of easy handling [Journal of the American Chemical Society, 85, 2149–2154 (1963); "Seikagaku Jikken Koza (Experimental biochemistry) Vol. 1, Chemistry of Proteins IV, Chemical Modification and Peptide Synthesis" ed. Nippon Seikagakkai, published by Tokyo Kagaku Dojin, Nov. 15, 1977, 207–495; "Zoku-Seikagaku Jikken Koza (Experimental biochemistry, second series) Vol. 2, Chemistry of Proteins, the last volume" ed. Nippon Seikagakkai, published by Tokyo Kagaku Dojin, May 20, 1987, 641–649, and the like].

The peptide (I) can be prepared using the solid phase technique in the following manner. The amino acid or amide thereof corresponding to the C-terminus of the desired peptide is firstly bound to a polymer which is insoluble in a reaction solvent (e.g. styrene/divinylbenzene copolymer, etc.) via an $\alpha$—COO— group or an $\alpha$—CONH— group which is formed by removing a hydrogen atom from $\alpha$-COOH group or $\alpha$-CONH$_2$ group contained in said amino acid or amide. To said amino acid or amide bound to the solid phase is further bound the next amino acid or peptide fragment in the direction towards the N-terminus of the desired peptide by condensation after protecting functional groups other than $\alpha$-COOH group (e.g $\alpha$-amino group), and then the protecting group for the amino group which is to be used for forming the peptide bond, i.e. $\alpha$-amino group in the amino acid or peptide fragment, is removed. The peptide chain is elongated by repeating the former procedure for binding the amino acid or peptide fragment and the latter procedure for removing the protecting group, alternately, thereby forming the peptide chain corresponding to the desired peptide. The peptide chain prepared above is then removed from the polymer and any protecting group is removed from the protected functional group to give the desired peptide, which is then further purified. Preferably, the removal of the peptide chain from the polymer and the removal of the protecting groups from the protected functional group are conducted simultaneously using hydrogen fluoride from the viewpoint of suppressing side reactions. The obtained peptide can be effectively purified by a reversed phase liquid chromatography.

The peptide (I) is capable of specifically binding to the anti-ATLA antibody, and hence, is useful as a reagent for detecting the anti-ATLA antibody formed after ATLV-infection.

The peptide (I) can be utilized for measuring the anti-ATLA antibody in the conventional methods such as immunofluorescence method, passive hemagglutination method, radioimmunoassay, ELISA, etc. These methods are well known to those skilled in the art. The use of the peptide of the present invention for measuring the anti-ATLA antibody is explained hereinbelow in more detail in case of ELISA.

The system comprises a carrier, the peptide (I) as a reagent, a blocking agent, a specimen to be determined, an antibody for labelling, an enzyme and a substrate. The carrier is coated with the peptide (I) and the peptide-coated carrier is then treated with the blocking agent to block non-specific protein binding sites on said carrier. To the peptide-coated carrier is added the specimen to be determined and then incubated. The carrier is further contacted with an enzyme-labelled antibody and incubated. To the carrier treated above is added the substrate and the mixture is incubated, followed by measuring an amount of the produced chromophore by an absorptiometer. The peptide (I) to be used for coating the carrier may be a single peptide or a combination of more than one peptide. The carrier is preferably a cup for ELISA or beads made of glass or resin. Prior to measurement, the peptide (I) is dissolved in 0.01M carbonate buffer and the solution is added, for example, to a cup for ELISA made of polystyrene, which is then allowed to stand at 4° C. overnight or at room temperature for 3 hours so that the surface of the carrier is coated with the peptide (I). The blocking agent for blocking non-specific protein binding sites on the carrier includes bovine serum albumine, casein, skimmed milk, serum derived from an immunized animal for obtaining an anti-human IgG antibody or an anti-human IgM antibody as the antibody for labelling, gelatin, and the like. The antibody for labelling includes an anti-human IgG antibody, an anti-human IgM antibody, and the like. The enzyme includes, for example, alkaline phosphatase, glucose oxidase, peroxidase, beta-galactosidase, and the like. Prior to measurement, preferably the enzyme is previously bound to the antibody for labelling by using a compound having at least two functional groups (e.g. glutaraldehyde, etc.) to form a conjugate. This preformed conjugate may be a part of the components of the system. The substrate is selected from those suitable to each enzyme used. For example, in case that the enzyme is peroxidase, then hydrogen peroxide and o-phenylenediamine and the like are preferably used.

The peptide (I) is also used as an adsorbent for the anti-ATLA antibody when immobilized on the carrier. In this case, the peptide (I) may be a single kind of peptide or may be used in a combination of more than one kind of peptides.

The carrier used for immobilizing the peptide (I) is preferably those having a hydrophilic surface and having reactive functional groups such as amino, carboxyl, hydroxyl, etc. for forming the covalent bond with the peptide. When the peptide (I) is used as the adsorbent for adsorbing the anti-ATLA antibody in a body fluid of patients with ATLV-associated diseases, it preferably has no solubility in the body fluid in addition to the above-mentioned properties. The carrier may be in any shape such as globe, granule, membrane, hollow fiber, fiber and the like. The carrier in the particulate shape such as globe and granule has a larger surface area capable of contacting with the target anti-ATLA antibody than that in the form of membrane, hollow fiber and fiber when packed in a column with the same volume, and hence, is preferable from the viewpoint of efficiency of adsorption of the anti-ATLA antibody. The carrier in the particulate shape has preferably a diameter ranging from 50 to 2,000 $\mu$m. When the particle size is smaller than 50 $\mu$m, the particles approach closer to each other, and as a result, cells in the body fluid tend to be clogged by the particles. When the particle size is larger than 2,000 μm, the area capable of contacting with the anti-ATLA antibody becomes smaller though cells do not tend to be clogged by the particles. Both particle sizes falling outside the above range are not preferable. Specific carrier includes an organic carrier such as a carrier made of cellulose [e.g. CM-Cellulofine CL (available from Seikagaku Kogyo Co., Ltd.), etc.], a carrier made of polyvinyl alcohol [e.g. TSK-gel CM-Toyopearl 650C (manufactured by Tosoh Corporation), etc.], an carrier made of agarose [Sepharose 4B, CM-Sepharose CL-6B (manufactured by Pharmacia-LKB, Sweden), etc.] and the like, and an inorganic carrier such as porous glass [e.g. CPG-10-1000 (manufactured by Electronucleonics, US), etc.].

The peptide (I) can be immobilized on the carrier according to the conventional method for immobilizing peptides or proteins on the carrier. Such method for immobilization includes, for example, an activated ester method in which carboxyl group on the carrier is converted into succinimidoxycarbonyl group by reaction with N-hydroxysuccinic acid imide and then the resulting succinimidoxycarbonyl group is reacted with amino group of the peptide (I); a condensation method in which the carrier is condensed with the peptide (I) by reacting amino group (or carboxyl group) on the carrier with carboxyl group (or amino group) of the peptide (I) in the presence of a condensating agent (e.g. dicyclohexylcarbodiimide, etc.); a cross-linking method in which the carrier and the peptide (I) are cross-linked to each other using a compound having two or more functional groups (e.g. glutaraldehyde, etc.), and the like. An adsorbent prepared by immobilizing the peptide (I) on the carrier according to the activated ester method is capable of adsorbing the anti-ATLA antibody with the highest efficiency.

The peptide (I) is immobilized on the carrier in an amount of about $1 \times 10^{-9}$ mol/g(carrier) or more so that the resulting adsorbent can adsorb a significant amount of the anti-ATLA antibody and preferably in an amount ranging from about $1 \times 10^{-7}$ to $5 \times 10^{-4}$ mol/g-(carrier) so that the peptide (I) immobilized on the carrier can be utilized effectively for adsorption of the anti-ATLA antibody.

The removal of the anti-ATLA antibody from the body fluid can be conducted by contacting the adsorbent prepared by immobilizing the peptide (I) on the carrier with blood, lymph, spinal fluid and the like containing the anti-ATLA antibody to adsorb the anti-ATLA antibody to the adsorbent. The adsorbent is used, for example, by being packed in a column. The column used for this purpose preferably has an inlet and an outlet having such a shape as being easily connected to a blood circuit and has filters made of polyesters etc. both between the inlet and the adsorbent layer and between the outlet and the adsorbent layer. The column is preferably made of polyethylene, polypropylene, polycarbonate, polyester, polymethacrylate and the like. Among these materials, polypropylene and polycarbonate are particularly preferable since they can be sterilized by autoclave sterilization, γ-ray sterilization and the like.

The removal of the anti-ATLA antibody from the column filled with the adsorbent prepared above can be carried out, for example, by an extracorporeal blood circulation system in which blood or plasma taken from blood vessel of the patient is passed through the column filled with the adsorbent, where the anti-ATLA antibody is removed from the blood or plasma by adsorption, and the blood or plasma which passed through the column is then brought back to the blood vessel.

In accordance with the present invention is provided the peptide (I) capable of specifically binding to the anti-ATLA antibody. The peptide (I) can provide a reagent for measuring the anti-ATLA antibody and an adsorbent capable of effectively adsorbing the anti-ATLA antibody.

The present invention is explained in more detail by the following Examples and Reference Examples but should not be construed to be limited thereto.

EXAMPLE 1

A peptide (I), wherein X is -Lys-Lys- and A is the peptide fragment (A-1), of the following amino acid sequence which is identified in the Sequence Listing as SEQ ID NO: 6:

H—Lys—Lys—Pro—Pro—Pro—Pro—Ser—Ser—Pro—Thr—His—

Asp—Pro—Pro—Asp—Ser—Asp—Pro—Gln—Ile—Pro—Pro—

Pro—Tyr—Val—Glu—Pro—Thr—Ala—Pro—Gln—Val—Leu—OH was synthesized by a solid phase method using an automatic peptide synthesizer (Model 430A manufactured by Applied Biosystems, US). A granular resin made of a styrene/divinylbenezene copolymer (154 mg; moler ratio of styrene/divylbenzene, 99:1) [PAM Leucine, t-Boc-L-Leu manufactured by Applied Biosystems, US] which contains 0.65 mmol/g(resin) of 4-[Nα-(t-butoxycarbonyl)-L-leucylphenylacetomethyl] group of the formula:

$$[(CH_3)_3CO-\underset{O}{\overset{\|}{C}}-NHCH-\underset{O}{\overset{\|}{C}}-OCH_2-\underset{}{\underset{}{\bigcirc}}-CH_2-\underset{O}{\overset{\|}{C}}-NHCH_2]$$

with CH(CH$_3$)$_2$ side chain was used as a solid phase. To the resin were bound the corresponding amino acids (L-alanine, L-aspartic acid, L-glutamine, L-glutamic acid, L-histidine, L-isoleucine, L-lysine, L-proline, L-serine, L-threonine, L-tyrosine and L-valine) successively in the direction towards the N-terminus of the desired peptide using the procedures listed in Table 1. In the condensation reaction, the above amino acids were used in the form of anhydrous N-(tert-butoxycarbonyl)-L-alanine, anhydrous N-(tert-butoxycarbonyl)-O-benzyl-L-aspartic acid, N-(tert-butoxycarbonyl)-L-glutamine-(1-benzotriazolyl) ester, anhydrous N-(tert-butoxycarbonyl)-O-benzyl-L-glutamic acid, N$^α$-(tert-butoxycarbonyl)-N$^{im}$-dinitrophenyl-L-histidine-(1-benzotriazolyl) ester, anhydrous N-(tert-butoxycarbonyl)-L-isoleucine, anhydrous N$^α$-(tert-butoxycarbonyl)-N$^ε$-2-chlorobenzyloxycarbonyl-L-lysine, anhydrous N-(tert-butoxycarbonyl)-L-proline, anhydrous N-(tert-butoxycarbonyl)-O-benzyl- L-serine, anhydrous N-(tert-butoxycarbonyl)-O-benzyl-L-threonine, anhydrous N$^\alpha$-(tert-butoxycarbnyl)-O-bromobenzyloxycarbonyl-L-tyrosine and anhydrous N-(tert-butoxycarbonyl)-L-valine in an amount of about tenfold molar amount of the substrate. The condensation reaction was conducted at room temperature. The reaction time varied depending on a kind of the amino acid to be condensed but was in a range of 10 to 20 minutes. After completion of the condensation reaction for all amino acids, the resulting resin was washed with diethyl ether, dichloromethane and methanol in this order on a glass filter and then dried in vacuum to give a dry resin (0.25 g). The dry resin (0.25 g) was then mixed with thiophenol (2 ml) and N,N-dimethylformamide (48 ml) in a glass flask and the mixture was stirred with a stirrer at room temperature for 30 minutes. The supernatent was separated and the same procedure was repeated three times. The resulting mixture was washed with dichloromethane and methanol and dried under reduced pressure to give a resin (0.2 g). The obtained dry resin (0.2 g) was mixed with anisole (0.3 ml) and ethyl methyl sulfide (0.05 ml) in a reaction vessel made of poly(trifluoromonochloroethylene) (HF-Reaction Apparatus type I manufactured by Peptide Kenkyusho K. K.) and to the mixture was added hydrogen fluoride (10 ml) at −20° C. and the mixture was stirred at the same temperature for 30 minutes and then at 0° C. for 30 minutes. From the reaction mixture were removed hydrogen fluoride, anisole and ethyl methyl fluoride under reduced pressure and the residue was washed sufficiently with diethyl ether on a glass filter. The obtained minutes. Mass spectrum by fast atomic bombardmend method (hereinafter referred to as "FAB method") showed 3527 of molecular weight of the purified peptide (theoretical value: 526.88).

TABLE 1

| Procedure | Solvent and/or reagent used | Time (sec) | Frequency |
|---|---|---|---|
| 1 Removal of tert-butoxy-carbonyl | Trifluoroacetic acid (6.6 ml) | 300 | 1 |
| 2 Washing | N,N-dimethylformamide | 40 | 1 |
| 3 Neutralization | N,N-dimethylformamide solution containing 20% by volume of di-isopropylethylamine | 60 | 1 |
| 4 Washing | N,N-dimethylformamide | 40 | 1 |
| 5 Condensation reaction | N,N-dimethylformamide solution containing an amino acid (10 to 25 ml) | 600 to 1200 | 1 |
| 6 Washing | N,N-dimethylformamide | 40 | 1 |

EXAMPLE 2

The procedure of Example 1 for synthesis on solid phase and purification of peptide was repeated to give a peptide (I), in which X is -Lys-Lys-Lys- and A is the peptide fragment (A-1), of the following amino acid sequence which is identified in the Sequence Listing as SEQ ID NO: 7:

A has the following amino acid sequence which is identified in the Sequence Listing as SEQ ID NO: 28:

—Pro—Pro—Pro—Pro—Ser—Ser—Pro—Thr—His—Asp—Pro—Pro—Asp—Ser—Asp

Pro—Gln—Ile—Pro

H—Lys—Lys—Lys—Pro—Pro—Pro—Pro—Ser—Ser—Pro—Thr—His—

Asp—Pro—Pro—Asp—Ser—Asp—Pro—Gln—Ile—Pro—OH.

residue was extracted with 2N aqueous acetic acid solution and the extract was lyophilized to give a crude peptide (120 mg). The obtained crude peptide was purified by preparative reversed phase high performance liquid chromatography [column: octadecylated silica gel (particle size: 15 μm) filled column (φ: 50 mm, length: 300 mm) manufactured by Nippon Waters K. K., μ BONDASPHERE 15μ C18-100 Å; mobile phase: a mixed solvent of water/acetonitrile containing 0.05% by volume of trifluoroacetic acid, a concentration of acetonitril was gradually changed from 24% by volume to 30% by volume over 18 minutes) to give a purified peptide (50 mg). The obtained purified peptide was subjected to analytical reversed phase high performance liquid chromatography [column: octadecylated silica gel (particle size: 5 μm) filled column (φ: 4 mm, length: 150 mm), TSK-gel ODS-80TM manufactured by Toso K. K.; mobile phase: a mixed solvent of water-/acetonitrile containing 0.05% by volume of trifluoroacetic acid, a concentration of acetonitrile was gradually changed from 5% by volume to 50% by volume over 30 minutes; flow rate: 1 ml/min.; detector: absorbance at 210 nm] to show a single sharp peak after 18.0

The obtained peptide was subjected to the same analytical reversed phase high performance liquid chromatography as in Example 1 t show a single sharp peak after 18.2 minutes. Mass spectrum showed by FAB method showed 2363 of molecular weight of the peptide (theoretical value: 2362.56).

EXAMPLE 3

The procedure of Example 1 for synthesis on solid phase and purification of peptide was repeated to give a peptide (I), in which X is -Lys-Lys-Lys-Lys-Lys- (this sequence is identified in the Sequence Listing as SEQ ID NO: 5), of the following amino acid sequence which is identified in the Sequence Listing as SEQ ID NO: 8:

The A moiety of SEQ ID NO: 8 has the following amino acid sequence which is identified in the Sequence Listing as SEQ ID NO: 29:

—Pro—Tyr—Val—Glu—Pro—Thr—Ala—Pro—Gln—Val—Leu—

H—Lys—Lys—Lys—Lys—Lys—Pro—Tyr—Val—Glu—Pro—Thr—Ala—

Pro—Gln—Val—Leu—OH.

The obtained peptide was subjected to the same analytical reversed phase high performance liquid chromatography as in Example 1 to show a single sharp peak after 19.3 minutes. Mass spectrum showed by FAB method showed 2239 of molecular weight of the peptide (theoretical value: 2238.72).

EXAMPLE 4

The procedure of Example 1 for synthesis on solid phase and purification of peptide was repeated to give a peptide (I), in which X is -Lys-Lys-Lys-, of the following amino acid sequence which is identified in the Sequence Listing a SEQ ID NO: 9 :

The A moiety of SEQ ID NO: 9 has the following amino acid sequence which is identified in the Sequence Listing as SEQ ID NO: 30:

—Pro—Val—Met—His—Pro—His—Gly—Ala—Pro—Pro—Asn—His—Arg—Pro—Trp—

Gln—Met—Lys—Asp—Leu—Gln—Ala—Ile—Lys—Gln—Glu—Val—Ser—Gln—Ala—

H—Lys—Lys—Lys—Pro—Val—Met—His—Pro—His—Gly—Ala—Pro—

Pro—Asn—His—Arg—Pro—Trp—Gln—Met—Lys—Asp—Leu—Gln—

Ala—Ile—Lys—Gln—Glu—Val—Ser—Gln—Ala—OH.

The obtained peptide was subjected to the same analytical reversed phase high performance liquid chromatography as in Example 1 to show a single sharp peak after 19.8 minutes. Mass spectrum showed by FAB method showed 3814 of molecular weight of the peptide (theoretical value: 3813.40).

EXAMPLE 5

The procedure of Example 1 for synthesis on solid phase and purification of peptide was repeated to give a peptide (I), in which X is -Lys-Lys-, of the following amino acid sequence which is identified in the Sequence Listing as SEQ ID NO: 10 :

The A moiety of SEQ ID NO: 10 has the following amino acid sequence which is identified in the Sequence Listing as SEQ ID NO: 31:

—Gly—Leu—Pro—Glu—Gly—Thr—Pro—Lsy—Asp—Pro—Ile—Leu—Arg—Ser—Leu—Ala—

Tyr—Ser—Asn—Ala—Asn—Lys—Glu—Cys—Gln—Lys—Leu—Leu—Gln—Ala—

H—Lys—Lys—Gly—Leu—Pro—Glu—Gly—Thr—Pro—Lys—Asp—Pro—

Ile—Leu—Arg—Ser—Leu—Ala—Tyr—Ser—Asn—Ala—Asn—Lys—

Glu—Cys—Gln—Lys—Leu—Leu—Gln—Ala—OH.

The obtained peptide was subjected to the same analytical reversed phase high performance liquid chromatography as in Example 1 to show a single sharp peak after 18.2 minutes. Mass spectrum showed by FAB method showed 3512 of molecular weight of the peptide (theoretical value: 3512.03).

EXAMPLE 6

The procedure of Example 1 for synthesis on solid phase and purification of peptide was repeated to give a peptide (I), in which X is -Lys-Lys-Lys-Lys-Lys-(this sequence is identified in the Sequence Listing as SEQ ID NO: 5), of the following amino acid sequence which is identified in the Sequence Listing as SEQ ID NO: 11:

The A moiety of SEQ ID NO: 11 has the following amino acid sequence which is identified in the Sequence Listing as SEQ ID NO: 32:

—Asp—Pro—Ile—Leu—Arg—Ser—Leu—Ala—Tyr—Ser—Asn—Ala—Asn—Lys—Glu—Cys—

Gln—Lys—Leu—

H—Lys—Lys—Lys—Lys—Lys—Asp—Pro—Ile—Leu—Arg—Ser—Leu—

Ala—Tyr—Ser—Asn—Ala—Asn—Lys—Glu—Cys—Gln—Lys—Leu—OH

The obtained peptide was subjected to the same analytical reversed phase high performance liquid chromatography as in Example 1 to show a single sharp peak after 16.5 minutes. Mass spectrum showed by FAB method showed 2933 of molecular weight of the peptide (theoretical value: 2932.48).

EXAMPLE 7

The procedure of Example 1 for synthesis on solid phase and purification of peptide was repeated to give a peptide (I), in which X is -Lys-Lys-, of the following amino acid sequence which is identified in the Sequence Listing as SEQ ID NO: 12:

The A moiety of SEQ ID NO: 12 has the following amino acid sequence which is identified in the Sequence Listing as SEQ ID NO: 33:

—Gly—Asp—Tyr—Ser—Pro—Ser—Cys—Cys—thr—Leu—Thr—Ile—Gly—Val—Ser—Ser—

Tyr—His—Ser—Lys—Pro—Cys—Asn—Pro—Ala—Gln—Pro—Val—Cys—Ser—

H—Lys—Lys—Gly—Asp—Tyr—Ser—Pro—Ser—Cys—Cys—Thr—Leu—

Thr—Ile—Gly—Val—Ser—Ser—Tyr—His—Ser—Lys—Pro—Cys—

Asn—Pro—Ala—Gln—Pro—Val—Cys—Ser—OH.

The obtained peptide was subjected to the same analytical reversed phase high performance liquid chromatography as in Example 1 to show a single sharp peak after 21.5 minutes. Mass spectrum showed by FAB method showed 3359 of molecular weight of the peptide (theoretical value: 3358.77).

EXAMPLE 8

The procedure of Example 1 for synthesis on solid phase and purification of peptide was repeated to give a peptide (I), in which X is -Lys-Lys-Lys-, of the following amino acid sequence which is identified in the Sequence Listing as SEQ ID NO: 13:

The A moiety of SEQ ID NO: 13 has the following amino acid sequence which is identified in the Sequence Listing as SEQ ID NO: 34:

—Thr—Lys—Lys—Pro—Asn—Arg—Asn—Gly—Gly—Gly—Tyr—Tyr—Ser—Ala—Ser—Tyr—

Ser—Asp—Pro—Cys—Ser—Leu—Lys—Cys—Pro—Tyr—Leu—

H—Lys—Lys—Lys—Thr—Lys—Lys—Pro—Asn—Arg—Asn—Gly—Gly—

Gly—Tyr—Tyr—Ser—Ala—Ser—Tyr—Ser—Asp—Pro—Cys—Ser—

Leu—Lys—Cys—Pro—tyr—Leu—OH.

The obtained peptide was subjected to the same analytical reversed phase high performance liquid chromatography as in Example 1 to show a single sharp peak after 16.8 minutes. Mass spectrum showed by FAB method showed 3355 of molecular weight of the peptide (theoretical value: 3354.78).

EXAMPLE 9

The procedure of Example 1 for synthesis on solid phase and purification of peptide was repeated to give a peptide (I), in which X is -Lys-Lys-Lys- and A is the peptide fragment (A-3), of the following amino acid sequence which is identified in the Sequence Listing as SEQ ID NO: 14:

H—Lys—Lys—Lys—Phe—Leu—Asn—Thr—Glu—Pro—Ser—Gln—Leu—

Pro—Pro—Thr—Ala—Pro—Pro—Leu—Leu—Pro—His—Ser—Asn—

Leu—Asp—His—Ile—OH.

The obtained peptide was subjected to the same analytical reversed phase high performance liquid chromatography as in Example 1 to show a single sharp peak after 20.3 minutes. Mass spectrum showed by FAB method showed 3261 of molecular weight of the peptide (theoretical value: 3261.74).

EXAMPLE 10

The procedure of Example 1 for synthesis on solid phase and purification of peptide was repeated to give a peptide (I), in which X is -Lys-Lys-Lys-Lys-(this sequence is identified in the Sequence Listing as SEQ ID NO: 4), of the following amino acid sequence which is identified in the Sequence Listing as SEQ ID NO: 15:

H—Lys—Lys—Lys—Lys—Thr—Pro—Leu—Leu—Try—Pro—Ser—Leu—

Ala—Leu—Pro—Ala—Pro—His—Leu—Thr—Leu—Pro—Phe—Asn—

Trp—Thr—His—Cys—Phe—Asp—Pro—Gln—Ile—Gln—OH.

The A moiety of SEQ ID NO: 15 has the following amino acid sequence which is identified in the Sequence Listing as SEQ ID NO: 35:

—Thr—Pro—Leu—Leu—Tyr—Pro—Ser—Leu—Ala—Leu—Pro—Ala—Pro—His—Leu—Thr—

Leu—Pro—Phe—Asn—Trp—Thr—His—cys—Phe--Asp—Pro—Gln—Ile—Gln—

The obtained peptide was subjected to the same analytical reversed phase high performance liquid chromatography as in Example 1 to show a single sharp peak after 21.3 minutes. Mass spectrum showed by FAB method showed 3944 of molecular weight of the peptide (theoretical value: 3944.60).

EXAMPLE 11

The procedure of Example 1 for synthesis on solid phase and purification of peptide was repeated to give a peptide (I), in which X is -Lys-Lys-, of the following amino acid sequence which is identified in the Sequence Listing as SEQ ID NO: 16

The A moiety of SEQ ID NO: 16 has the following amino acid sequence which is identified in the Sequence Listing as SEQ ID NO: 36:

—Thr—Pro—Cys—His—asn—Ser—Leu—Ile—Leu—Pro—Pro—Phe—Ser—Leu—Ser—Pro—

Val—Pro—Thr—Leu—Gly—Ser—Arg—Ser—Arg—Arg—Ala—Val—Pro—Val—Ala—

H—Lys—Lys—Thr—Pro—Cys—His—Asn—Ser—Leu—Ile—Leu—Pro—

Pro—Phe—Ser—Leu—Ser—Pro—Val—Pro—Thr—Leu—Gly—Ser—

Arg—Ser—Arg—Arg—Ala—Val—Pro—Val—Ala—OH.

The obtained peptide was subjected to the same analytical reversed phase high performance liquid chromatography as in Example 1 to show a single sharp peak after 19.8 minutes. Mass spectrum showed by FAB method showed 3426 of molecular weight of the peptide (theoretical value: 3426.04).

EXAMPLE 12

The procedure of Example 1 for synthesis on solid phase and purification of peptide was repeated to give a peptide (I), in which X is -Lys-Lys-Lys-, of the following amino acid sequence which is identified in the Sequence Listing as SEQ ID NO: 17:

H—Lys—Lys—Lys—Val—Asp—Lys—Asp—Ile—Ser—Gln—Leu—Thr—

Gln—Ala—Ile—Val—Lys—Asn—His—Lys—Asn—Leu—Leu—Lys—

Ile—Ala—Gln—Tyr—Ala—Ala—Gln—Asn—Arg—Arg—Gly—Leu—

Asp—Leu—Leu—Phe—OH.

The A moiety of SEQ ID NO: 17 has the following amino acid sequence which is identified in the Sequence Listing as SEQ ID NO: 37:

—Val—Asp—Lys—Asp—Ile—Ser—Gln—Leu—Thr—Gln—Ala—Ile—Val—Lys—Asn—His—

Lys—Asn—Leu—Leu—Lys—Ile—Ala—Gln—Tyr—ALa—Ala—Gln—Asn—Arg—Arg—Gly—

Leu—Asp—Leu—Leu—Phe—

The obtained peptide was subjected to the same analytical reversed phase high performance liquid chromatography as in Example 1 to show a single sharp peak after 19.4 minutes. Mass spectrum showed by FAB method showed 4260 of molecular weight of the peptide (theoretical value: 4261.41).

EXAMPLE 13

The procedure of Example 1 for synthesis on solid phase and purification of peptide was repeated to give a peptide (I), in which X is -Lys-Lys, of the following amino acid sequence which is identified in the Sequence Listing as SEQ ID NO: 18 :

The A moiety of SEQ ID NO: 18 has the following amino acid sequence which is identified in the Sequence Listing as SEQ ID NO: 38:

—Cys—Arg—Phe—Pro—Asn—Ile—Thr—Asn—Ser—His—Val—Pro—Ile—Leu—Gln—Glu—

Arg—Pro—Pro—Leu—Glu—Asn—Arg—Val—Leu—Thr—Gly—Trp—Gly—Leu—

H—Lys—Lys—Cys—Arg—Phe—Pro—Asn—Ile—Thr—Asn—Ser—His—

Val—Pro—Ile—Leu—Gln—Glu—Arg—Pro—Pro—Leu—Glu—Asn—

Arg—Val—Leu—Thr—Gly—Trp—Gly—Leu—OH.

The obtained peptide was subjected to the same analytical reversed phase high performance liquid chromatography as in Example 1 to show a single sharp peak after 20.3 minutes. Mass spectrum showed by FAB method showed 3714 of molecular weight of the peptide (theoretical value: 3714.27).

EXAMPLE 14

The procedure of Example 1 for synthesis on solid phase and purification of peptide was repeated to give a peptide (I), in which X is -Lys-Lys-Lys-, of the following amino acid sequence which is identified in the Sequence Listing as SEQ ID NO: 19:

H—Lys—Lys—Lys—Leu—Ala—Gly—Pro—Cys—Ile—Leu—Arg—Gln—

Leu—Arg—His—Leu—Pro—Ser—Arg—Val—Arg—Tyr—Pro—His—

Tyr—Ser—Leu—Ile—Lys—Pro—Glu—Ser—Ser—Leu—OH.

The A moiety of SEQ ID NO: 19 has the following amino acid sequence which is identified in the Sequence Listing as SEQ ID NO: 39:

—Leu—Ala—Gly—Pro—Cys—Ile—Leu—Arg—Gln—Leu—Arg—His—Leu—Pro—Ser—Arg—

Val—Arg—Tyr—Pro—His—Tyr—Ser—Leu—Ile—Lys—Pro—Glu—Ser—Ser—Leu—

The obtained peptide was subjected to the same analytical reversed phase high performance liquid chromatography as in Example 1 to show a single sharp peak after 17.1 minutes. Mass spectrum showed by FAB method showed 3986 of molecular weight of the peptide (theoretical value: 3985.76).

EXAMPLE 15

The procedure of Example 1 for synthesis on solid phase and purification of peptide was repeated to give a peptide (I), in which X is -Lys-Lys- and A is the peptide fragment (A-2), of the following amino acid sequence which is identified in the Sequence Listing as SEQ ID NO: 20:

H—Lys—Lys—Tyr—Ala—Ala—Gln—Asn—Arg—Arg—Gly—Leu—Asp—

Leu—Leu—Phe—Trp—Glu—Gln—Gly—Gly—Leu—OH.

The obtained peptide was subjected to the same analytical reversed phase high performance liquid chromatography as in Example 1 to show a single sharp peak after 21.6 minutes. Mass spectrum showed by FAB method showed 2464 of molecular weight of the peptide (theoretical value: 2463.78).

EXAMPLE 16

The procedure of Example 1 for synthesis on solid phase and purification of peptide was repeated to give a peptide (I), in which X is -Lys-Lys-, of the following amino acid sequence which is identified in the Sequence Listing as SEQ ID NO: 21:

The A moiety of SEQ ID NO: 21 has the following amino acid sequence which is identified in the Sequence Listing as SEQ ID NO: 40:

—Leu—Leu—Pro—His—Ser—Asn—Leu—Asp—His—Ile—Leu—Glu—Pro—Ser—Ile—Pro—

Trp—Lys—Ser—Lys—

H—Lys—Lys—Leu—Leu—Pro—His—Ser—Asn—Leu—Asp—His—Ile—

Leu—Glu—Pro—Ser—Ile—Pro—Trp—Lys—Ser—Lys—OH.

The obtained peptide was subjected to the same analytical reversed phase high performance liquid chromatography as in Example 1 to show a single sharp peak after 17.6 minutes. Mass spectrum showed by FAB method showed 2581 of molecular weight of the peptide (theoretical value: 2581.00).

EXAMPLE 17

The procedure of Example 1 for synthesis on solid phase and purification of peptide was repeated to give a peptide (I), in which X is -Lys-Lys-Lys-Lys-(this sequence is identified in the Sequence Listing as SEQ ID NO: 4) and A is the peptide fragment (A-2), of the following amino acid sequence which is identified in the Sequence Listing as SEQ ID NO: 22:

H—Lys—Lys—Lys—Lys—Tyr—Ala—Ala—Gln—Asn—Arg—Arg—Gly—

Leu—Asp—Leu—Leu—Phe—Trp—Glu—Gln—Gly—Gly—Leu—OH.

The obtained peptide was subjected to the same analytical reversed phase high performance liquid chromatography as in Example 1 to show a single sharp peak after 19.8 minutes. Mass spectrum showed by FAB method showed 2720 of molecular weight of the peptide (theoretical value: 2720.12).

EXAMPLE 18

The procedure of Example 1 for synthesis on solid phase and purification of peptide was repeated to give a peptide (I), in which X is -Lys-Lys-Lys-Lys-Lys-(this sequence is identified in the Sequence Listing as SEQ ID NO: 5) and A is the peptide fragment (A-2), of the following amino acid sequence which is identified in the Sequence Listing as SEQ ID NO: 23:

H—Lys—Lys—Lys—Lys—Lys—Tyr—Ala—Ala—Gln—Asn—Arg—Arg—

Gly—Leu—Asp—Leu—Leu—Phe—Trp—Glu—Gln—Gly—Gly—Leu—OH.

The obtained peptide was subjected to the same analytical reversed phase high performance liquid chromatography as in Example 1 to show a single sharp peak after 18.0 minutes. Mass spectrum showed by FAB method showed 2977 of molecular weight of the peptide (theoretical value: 2976.46).

REFERENCE EXAMPLE 1

The procedure of Example 1 for synthesis on solid phase and purification of peptide was repeated to give a peptide (I), in which X is deleted and A is the peptide fragment (A-1), of the following amino acid sequence which is identified in the Sequence Listing as SEQ ID NO: 24:

H—Pro—Pro—Pro—Pro—Ser—Ser—Pro—Thr—His—Asp—

Pro—Pro—Asp—Ser—Asp—Pro—Gln—Ile—Pro—Pro—

Pro—Tyr—Val—Glu—Pro—Thr—Ala—Pro—Gln—Val—

Leu—OH.

The obtained peptide was subjected to the same analytical reversed phase high performance liquid chromatography as in Example 1 to show a single sharp peak after 19.3 minutes. Mass spectrum showed by FAB method showed 3271 of molecular weight of the peptide (theoretical value: 3270.54).

REFERENCE EXAMPLE 2

The procedure of Example 1 for synthesis on solid phase and purification of peptide was repeated to give a peptide (I), in which X is deleted, of the following amino acid sequence which is identified in the Sequence Listing as SEQ ID NO: 25:

H—Leu—Leu—Pro—His—Ser—Asn—Leu—Asp—His—Ile—Leu—Glu—

Pro—Ser—Ile—Pro—Trp—Lys—Ser—Lys—O H.

The obtained peptide was subjected to the same analytical reversed phase high performance liquid chromatography as in Example 1 to show a single sharp peak after 19.4 minutes. Mass spectrum showed by FAB method showed 2289 of molecular weight of the peptide (theoretical value: 2289.00).

REFERENCE EXAMPLE 3

The procedure of Example 1 for synthesis on solid phase and purification of peptide was repeated to give a peptide (I), in which X is deleted and A is the peptide fragment (A-2), of the following amino acid sequence which is identified in the Sequence Listing as SEQ ID NO: 26:

H—Tyr—Ala—Ala—Gln—Asn—Arg—Arg—Gly—Leu—Asp—

Leu—Leu—Phe—Trp—Glu—Gln—Gly—Gly—Leu—OH.

The obtained peptide was subjected to the same analytical reversed phase high performance liquid chromatography as in Example 1 to show a single sharp peak after 23.3 minutes. Mass spectrum showed by FAB method showed 2208 of molecular weight of the peptide (theoretical value: 2207.44).

REFERENCE EXAMPLE 4

The procedure of Example 1 for synthesis on solid phase and purification of peptide was repeated to give a peptide (I), in which X is deleted and A is the peptide fragment (A-3), of the following amino acid sequence which is identified in the Sequence Listing as SEQ ID NO: 27:

H—Phe—Leu—Asn—Thr—Glu—Pro—Ser—Gln—Leu—Pro—

Pro—Thr—Ala—Pro—Pro—Leu—Leu—Pro—His—Ser—

Asn—Leu—Asp—His—Ile—OH.

The obtained peptide was subjected to the same analytical reversed phase high performance liquid chromatography as in Example 1 to show a single sharp peak after 15.6 minutes. Mass spectrum showed by FAB method showed 2824 of molecular weight of the peptide (theoretical value: 2823.74).

EXAMPLE 19

Specimens:

ATLV-carrier serum (20 specimens)
Normal human serum (10 specimens)

ELISA

Each serum specimen was assayed for the presence of the anti-ATLA antibody by the following ELISA in which an absorbance was measured.

The peptide prepared in Example 1 or the peptide prepared in Reference Example 1 were each dissolved in 0.01M carbonate buffer (pH 9.5). Each 100 μl of the resulting peptide solution was added to a cup for ELISA made of polystyrene (manufactured by Dainatech) and the mixture was allowed to stand at 37° C. for 3 hours so that the peptide was coated on the cup. The cups were then washed with a 0.01M phosphate-buffered saline (hereinafter referred to as "PBS") containing 0.05% by volume of Tween 20 (×4). Then, to each cup was added PBS (150 μl) containing 20% by volume of goat serum and the mixture was allowed to stand at room temperature for 3 hours to block non-specific binding sites. The cups were then washed with PBS containing 0.05% by volume of Tween 20 (×4).

After each 100 μl of PBS containing 10% by volume of normal goat serum was added to each cup as a diluent for serum, each serum specimen (20 specimens of the ATLV-carrier serum and 10 specimens of the normal human serum) was added at a ratio of 8:1 (diluent : specimen; v/v). The mixtures were incubated at 37° C. for 1 hour and the cups were washed with PBS containing 0.05% by volume of Tween 20 (×4).

To each resulting assay cup was added PBS containing horseradish peroxidase conjugated goat anti-human IgG antibody (diluted at an optimal concentration with PBS containing 10% by volume of normal goat serum; 100 μl). After incubation at 37° C. for 30 minutes, these cups were washed with PBS containing 0.05% by volume of Tween 20 (×4). To each resulting assay cup was added a substrate [o-phenylenediamine dissolved in 0.1M citrate/phosphate buffer containing 0.02% by volume of hydrogen peroxide (pH 5.6) at a concentration of 0.3% by weight; 100 μl]. After the mixtures were allowed to stand at room temperature for 15 minutes, to each mixture was added 1N sulfuric acid (100 μl) to stop the reaction and an absorbance at 492 nm ($OD_{492}$) of each reaction solution was measured.

RESULTS

Figure 1A:
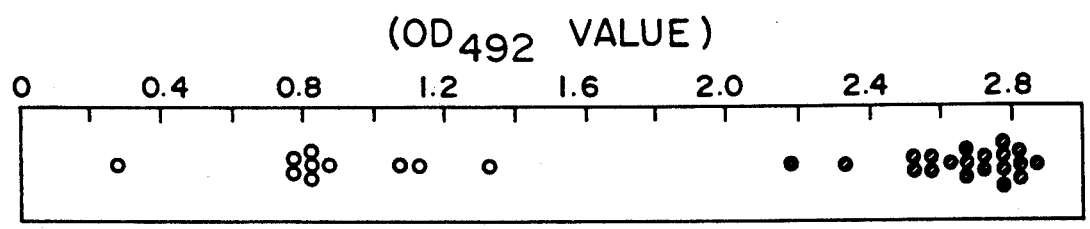
FIGS. 1a and 1b are graphs showing distribution of the $OD_{492}$ values obtained from each serum specimen by the method described in Example 19 using the peptide prepared in Example 1 and the peptide prepared in Reference Example 1, respectively.
Figure 1B:
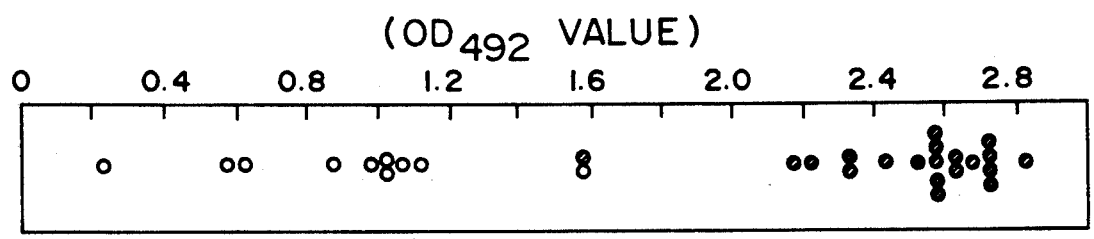
Figure 2A:
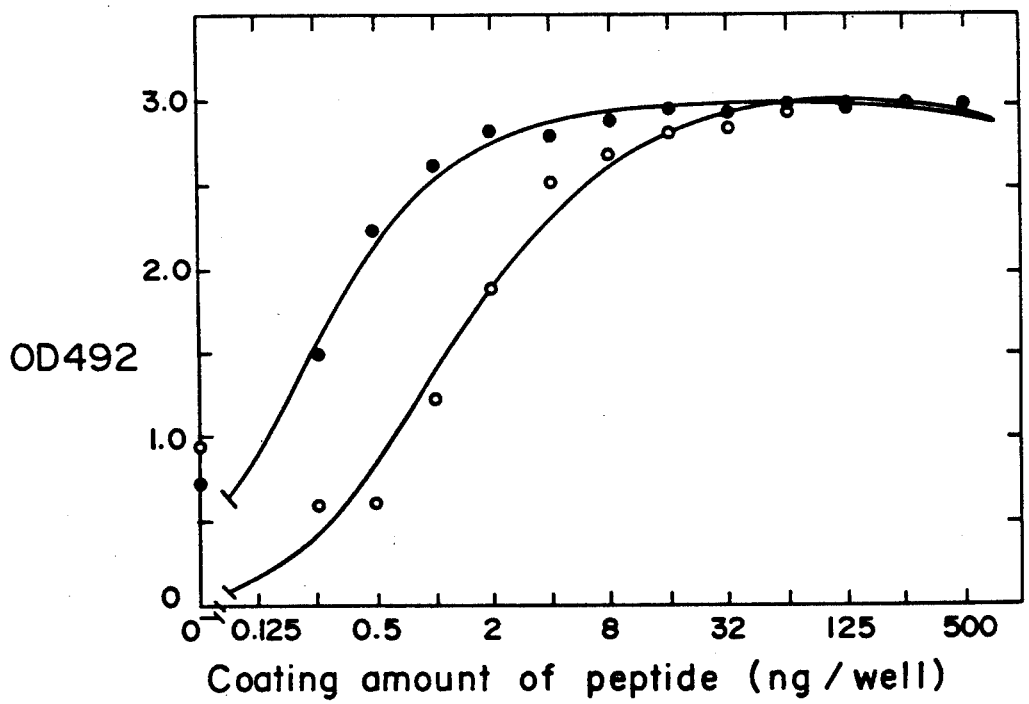
Figure 2B:
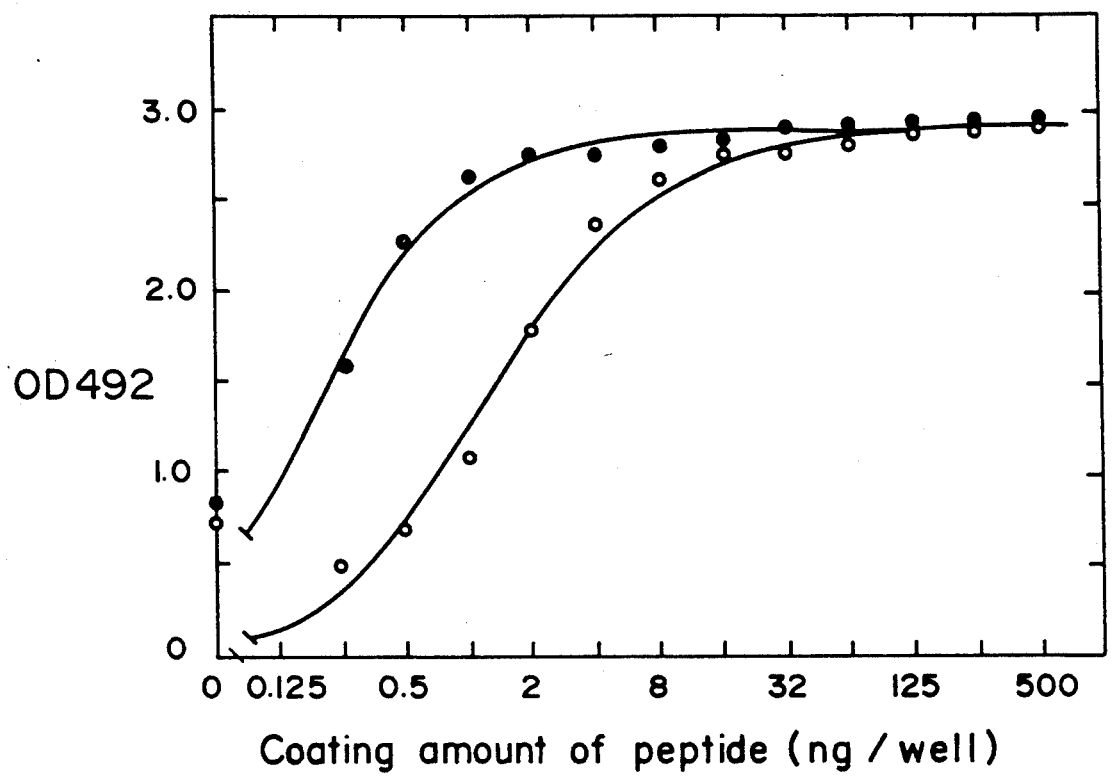
Figure 2C:
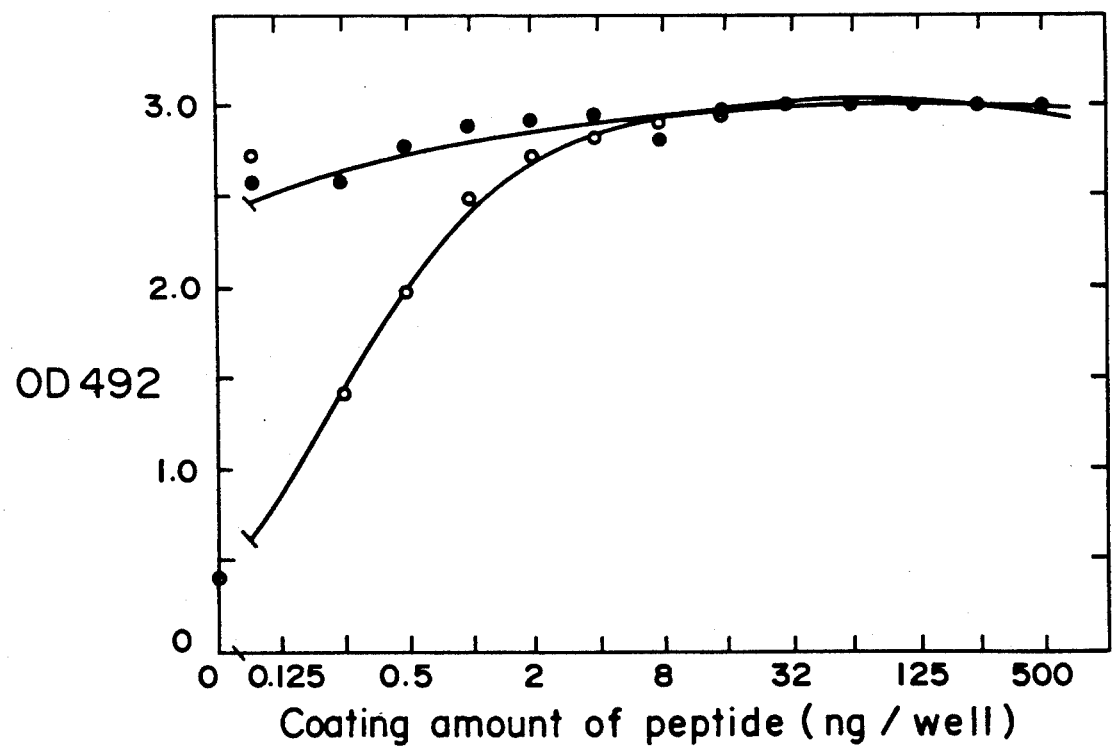
Figure 2D:
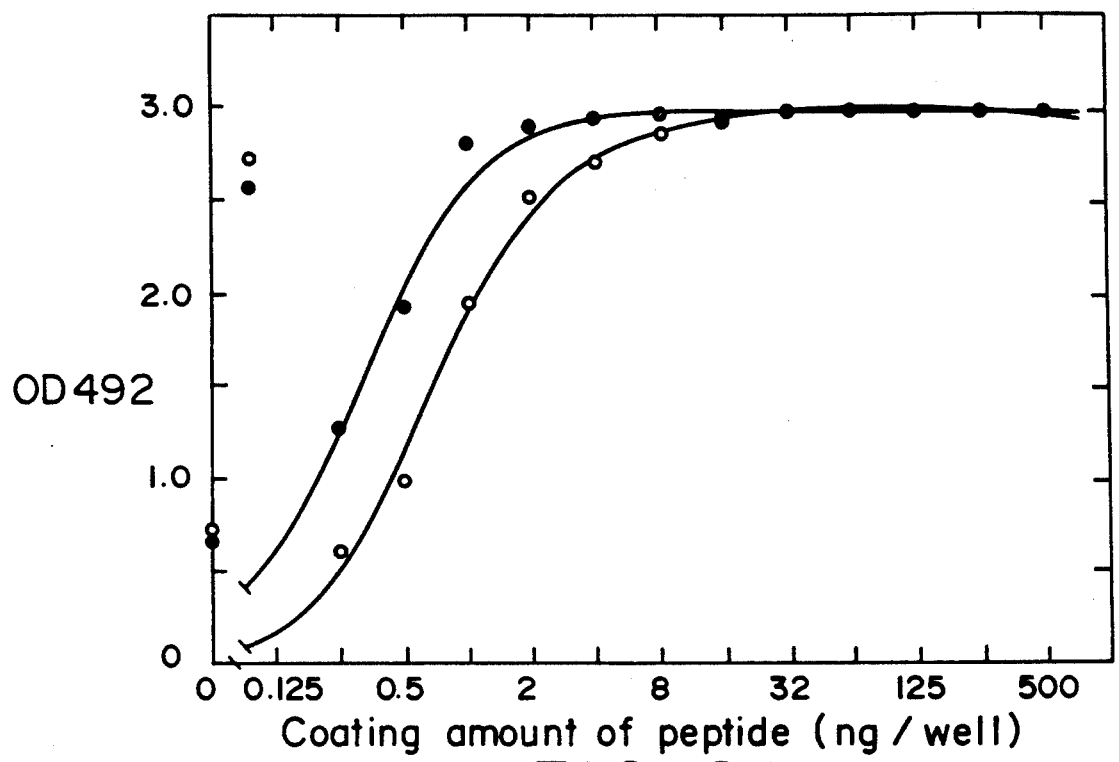
Figure 2E:
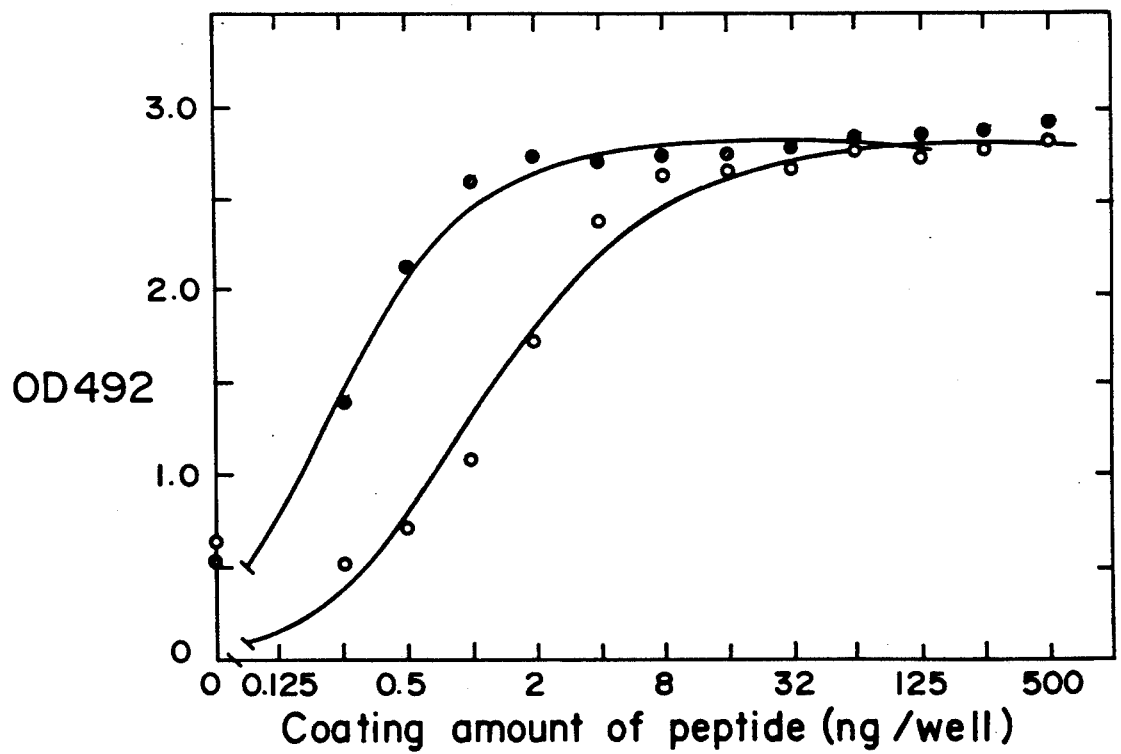
Figure 2F:
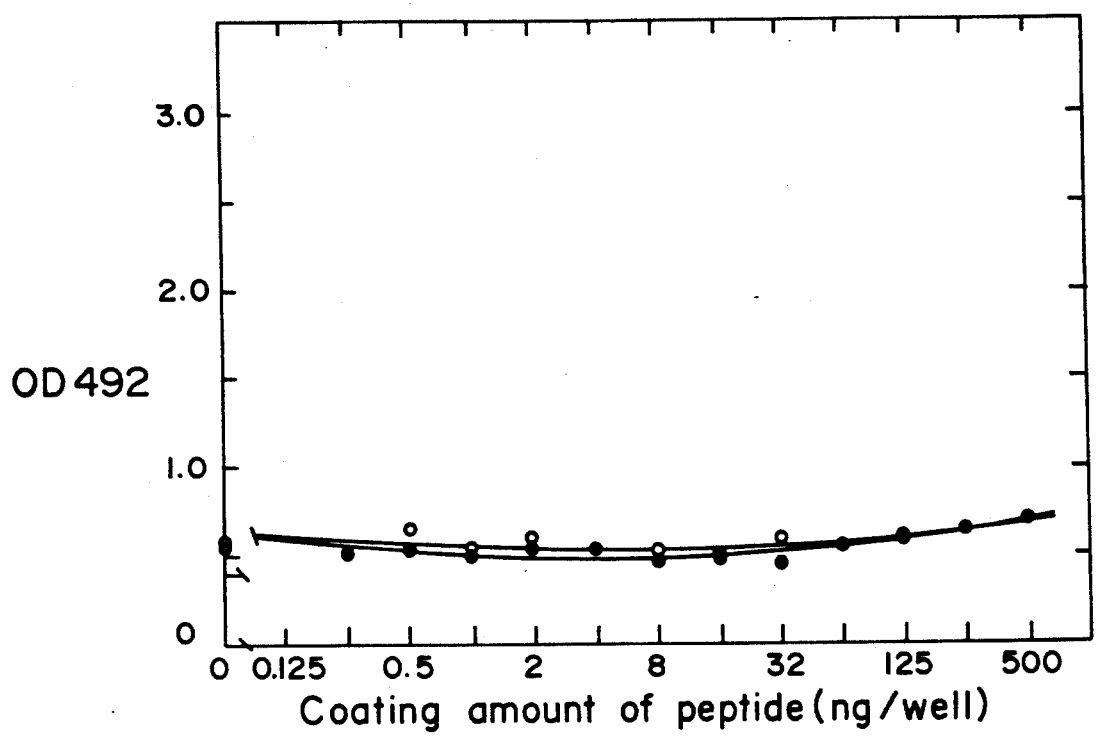
Figure 2G:
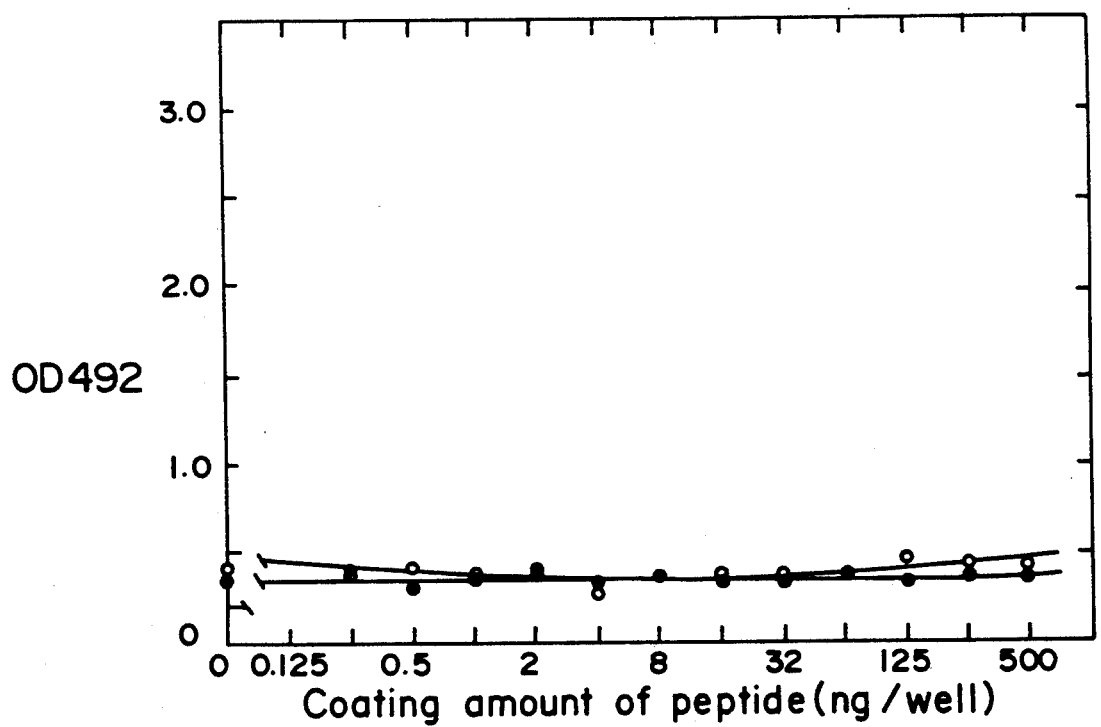

The results are shown in Table 2a and Table 2b for the peptide prepared in Example 1 and the peptide prepared in Reference Example 1, respectively. FIGS. 1a and 1b show distributions of the $OD_{492}$ values in Table 2a and Table 2b, respectively, wherein the $OD_{492}$ values obtained from the ATLV-carrier were shown as a closed circle and the $OD_{492}$ values obtained from the normal human serum were shown as an open circle. Cutoff value was determined using the $OD_{492}$ values of the ten normal human serums and used for determination as to whether the specimens are positive or negative for the anti-ATLA antibody. The cutoff value was calculated by the equation: cutoff value = ((mean value of $OD_{492}$ values of the normal human serum) +2SD). When the presence of the anti-ATLA antibody in each serum specimen was assayed using this cutoff value, all ATLV-carrier serums were determined to be positive and all normal human serums were determined to be negative.

From the results shown in Tables 2a and 2b and FIGS. 1a and 1b, it can be seen that the absorbance at 492 nm of the reaction solution in case of the peptide prepared in Example 1 is on the average smaller than that of the peptide prepared in Reference Example 1 when the specimen is the normal human serum. This shows the absence of the reaction induced by non-specific absorbance of antibodies other than the anti-ATLA antibody in serum (e.g. human IgG antibody) in case that the carrier coated with the peptide prepared in Example 1 is used.

TABLE 2a

| Normal human serum | | ATLV-carrier serum | | | |
|---|---|---|---|---|---|
| Serum No. | OD$_{492}$ | Serum No. | OD$_{492}$ | Serum No. | OD$_{492}$ |
| 1 | 0.761 | 1 | 2.651 | 11 | 2.802 |
| 2 | 1.051 | 2 | 2.670 | 12 | 2.719 |
| 3 | 0.845 | 3 | 2.596 | 13 | 2.899 |
| 4 | 0.260 | 4 | 2.850 | 14 | 2.786 |
| 5 | 0.796 | 5 | 2.586 | 15 | 2.542 |
| 6 | 0.847 | 6 | 2.755 | 16 | 2.622 |
| 7 | 1.311 | 7 | 2.833 | 17 | 2.531 |
| 8 | 0.832 | 8 | 2.733 | 18 | 2.193 |
| 9 | 1.112 | 9 | 2.779 | 19 | 2.656 |
| 10 | 0.891 | 10 | 2.783 | 20 | 2.317 |
| Mean | 0.871 | — | | | |
| SD | 0.275 | — | | | |
| Cutoff value | | 1.420 | | | |

TABLE 2b

| Normal human serum | | ATLV-carrier serum | | | |
|---|---|---|---|---|---|
| Serum No. | OD$_{492}$ | Serum No. | OD$_{492}$ | Serum No. | OD$_{492}$ |
| 1 | 0.953 | 1 | 2.230 | 11 | 2.748 |
| 2 | 1.026 | 2 | 2.441 | 12 | 2.844 |
| 3 | 0.642 | 3 | 2.558 | 13 | 2.618 |
| 4 | 0.248 | 4 | 2.653 | 14 | 2.594 |
| 5 | 0.854 | 5 | 2.589 | 15 | 2.161 |
| 6 | 0.568 | 6 | 2.587 | 16 | 2.591 |
| 7 | 1.111 | 7 | 2.304 | 17 | 2.324 |
| 8 | 1.018 | 8 | 2.739 | 18 | 2.558 |
| 9 | 1.552 | 9 | 2.740 | 19 | 2.628 |
| 10 | 1.057 | 10 | 2.722 | 20 | 1.594 |
| Mean | 0.903 | — | | | |
| SD | 0.354 | — | | | |
| Cutoff value | | 1.612 | | | |

EXAMPLE 20

Specimens

ATLV-carrier serum (5 specimens)
Normal human serum (2 specimens)

ELISA

Using five specimens of ATLV-carrier serum which are optionally selected from the ten specimens determined to be positive in Example 19 and two specimens of normal human serum which are optionally selected from the ten specimens determined to be negative in Example 19, an absorbance was measured by the following ELISA to assay an optimal coating amount of the peptide for determining the presence of the anti-ATLA antibody.

The peptide prepared in Example 1 or the peptide prepared in Reference Example 1 were each dissolved in 0.01M carbonate buffer (pH 9.5) at a concentration of 0 to 320 μg/ml. Each 100 μl of the resulting peptide solution was added to a cup for ELISA made of polystyrene (the same as mentioned above) and the mixture was allowed to stand at 4° C. overnight so that the peptide is coated on the cup. The cups were then washed with PBS containing 0.05% by volume of Tween 20 (×3) and then with PBS (×1). Then, to each cup was added PBS (150 μl) containing 20% by volume of normal goat serum and the mixture was allowed to stand at room temperature for 3 hours to block non-specific binding sites. The cups were then washed with PBS containing 0.05% by volume of Tween 20 (×4) and then with PBS (×1).

After each 100 μl of PBS containing 10% by volume of normal goat serum was added to each cup as a diluent, each serum specimen (5 specimens of the ATLV-carrier serum and 2 specimens of the normal human serum; hereinafter optionally referred to as "serum No. 1" to "serum No. 7", respectively) was added at a ratio of 8:1 (diluent:specimen; v/v). The mixtures were incubated at 37° C. for 1 hour and the cups were washed with PBS containing 0.05% by volume of Tween 20 (×3) and then with PBS (×1).

To each resulting assay cup was added PBS containing horseradish peroxidase conjugated goat anti-human IgG antibody (diluted at an optimal concentration with PBS containing 10% by volume of normal goat serum; 100 μl). After incubation at 37° C. for 30 minutes, these cups were washed with PBS containing 0.05% by volume of Tween 20 (×3) and then with PBS (×1). To each resulting assay cup was added a substrate [o-phenylenediamine dissolved in 0.1M citrate/phosphate buffer containing 0.02% by volume of hydrogen peroxide (pH 5.6) at a concentration of 0.3% by weight; 100 μl]. After the mixtures were allowed to stand at room temperature for 20 minutes, to each mixture was added 1N sulfuric acid (100 μl) to stop the reaction and an absorbance at 492 nm (OD$_{492}$) of each reaction solution was measured.

Results

The results are shown in FIGS. 2a, 2b, 2c, 2d, 2e, 2f and 2g for the serums No. 1 to No. 7, respectively. These Figures show OD$_{492}$ values at varying coated amounts of the peptide in each serum specimen wherein the OD$_{492}$ values for each serum specimen using the peptide prepared in Example 1 were shown as a closed circle and the OD$_{492}$ values for each serum specimen using the peptide prepared in Reference Example 1 were shown as an open circle. In ELISA using the peptide prepared in Example 1 for five serum specimens which were determined to be positive in Example 19 (serums No. 1 to No.5), the peptide amount of more than 0.2 ng/well gave the OD$_{492}$ value with which the specimen can be determined to be positive and the peptide amount of 1 ng/well gave a maximum OD$_{492}$ value. On the other hand, in ELISA using the peptide prepared in Reference Example 1 for the same serum specimens, the peptide amount of more than 1 ng/well was necessary for the specimen to be determined to be positive and the peptide amount of more than 10 ng/well was necessary for obtaining a maximum OD$_{492}$ value. In case of the two specimens which were determined to be negative in Example 19 (serums No. 6 to No. 7), the OD$_{492}$ value with which the specimen can be determined to be negative was obtained at any coated amount of the peptide in both peptides. This shows that, by adding the peptide fragment represented by X to the viral antigenic polypeptide moiety represented by A in the general formula (I), the sensitivity of the ELISA using said viral antigenic polypeptide was raised by more than tenfold.

EXAMPLE 21

Specimens

ATLV-carrier serum (5 specimens)
ATLV-false-positive serum (5 specimens)
Normal human serum (10 specimens)

ELISA

Each serum specimen was assayed for the presence of the anti-ATLA antibody by the following ELISA in which an absorbance was measured.

The peptide prepared in Example 1 was diluted in 0.01M carbonate buffer (pH 9.5). Each 100 μl of the resulting peptide solution was added to a cup for ELISA made of polystyrene (the same as mentioned above) and the mixture was allowed to stand at room temperature for 3 hours so that the peptide is coated on the cup. After removing the peptide solution in the cups, and to each cup was added PBS (200 μl) containing 20% by volume of normal goat serum and the mixture was allowed to stand at room temperature for 3 hours to block non-specific protein-binding sites on the carrier. Thereafter, the first portion of the obtained assay cups was immediately subjected to ELISA. The second portion of the assay cups was sealed while maintaining the blocking solution used for blocking and stored at 4° C. As to the remaining portion of the assay cups, the blocking solution used for blocking was removed, the cup was allowed to stand at room temperature for drying and sealed in the same way and then stored at 4° C.

ELISA was conducted in the following manner. The assay cup to be immediately subjected to measurement after blocking and the assay cup stored at 4° C. while maintaining the blocking solution were washed, after removing the blocking solution, with PBS containing 0.05% by volume of Tween 20 (×3) and then with PBS (×1) and subjected to the reaction with each serume specimen. The assay cup stored at 4° C. after removing the blocking solution and drying was directly subjected to the reaction with each serum specimen without washing in the following manner.

After each 100 μl of PBS containing 10% by volume of normal goat serum was added to each cup as a diluent, each serum specimen (5 specimens of the ATLV-carrier serum, 5 specimens of ATLV false positive serum and 5 specimens of the normal human serum) was added at a ratio of 20:1 (diluent:specimen; v/v). The mixtures were incubated at 37° C. for 1 hour and the cups were washed with PBS containing 0.05% by volume of Tween 20 (×3) and then with PBS devoid of Tween 20 (×1).

To each resulting assay cup was added PBS containing horseradish peroxidase conjugated goat anti-human IgG antibody (diluted at an optimal concentration with PBS containing 10% by volume of normal goat serum; 100 μl). After incubation at 37° C. for 30 minutes, these cups were washed with PBS containing 0.05% by volume of Tween 20 (×3) and then with PBS (×1). To each resulting assay cup was added a substrate [o-phenylenediamine dissolved in 0.1M citrate/phosphate buffer containing 0.02% by volume of hydrogen peroxide (pH 5.6) at a concentration of 0.3% by weight; 100 μl]. After the mixtures were allowed to stand at room temperature for 20 minutes, to each mixture was added 1N sulfuric acid (100 μl) to stop the reaction and an absorbance at 492 nm ($OD_{492}$) of each reaction solution was measured.

Results

The results are shown in FIGS. 3a, 3b and 3c as a distribution of the values. FIG. 3a shows the results as a distribution of the values using the assay cup coated with the peptide prepared in Example 1 which was immediately subjected to the measurement after blocking. FIG. 3b shows the results as a distribution of the values using the assay cup coated with the peptide which was stored at 4° C. while maintaining the blocking solution after blocking. FIG. 3c shows the results as a distribution of the values using the assay cup coated with the peptide which was stored at 4° C. after removing the blocking solution and drying. In FIGS. 3a, 3b and 3c, the $OD_{492}$ values obtained from the ATLV-carrier were shown as a closed circle, the $OD_{492}$ obtained from the false positive serum were shown as an open circle and the $OD_{492}$ values obtained from the normal human serum were shown as a cross. Cutoff value was determined using the $OD_{492}$ values of the five normal human serums and used for determination as to whether the specimens are positive or negative for the anti-ATLA antibody. The cutoff value was calculated by the equation: cutoff value = ((mean value of $OD_{492}$ values of the normal human serum) +2SD). When the presence of the anti-ATLA antibody in each serum specimen was assayed using this cutoff value, all ATLV-carrier serums were determined to be positive and all ATLV-false-positive serums and normal human serums were determined to be negative.

From the results shown above, the ELISA using the peptide of the present invention has 100% corelation with the indirect immunofluorescence method which is known as presently the most sure method for determining the presence of the anti-ATLA antibody.

EXAMPLE 22

Specimens

ATLV-carrier serum (20 specimens)
Normal human serum (10 specimens)

ELISA

Each serum specimen was assayed for the presence of the anti-ATLA antibody by the following ELISA in which an absorbance was measured.

The peptide prepared in Example 15 or the peptide prepared in Example 16 were each diluted in 0.01M carbonate buffer (pH 9.5). Each 100 μl of the resulting peptide solution was added to a cup for ELISA made of polystyrene (the same as mentioned above) and the mixture was allowed to stand at 4° C. overnight so that the peptide is coated on the cup. The cups were then washed with PBS containing 0.05% Tween 20 (×4). Then, to each cup was added PBS (200 μl) containing 20% by volume of normal goat serum and the mixture was allowed to stand at room temperature for 3 hours to block non-specific protein binding sites. The cups were then washed with PBS containing 0.05% by volume of Tween 20 (×4).

Thereafter, the procedure as in Example 19 was repeated and an absorbance at 492 nm ($OD_{492}$) of each reaction solution was measured.

Results

The results are shown in Table 3a and Table 3b for the peptide prepared in Example 15 and the peptide prepared in Example 16, respectively. FIGS. 4a and 4b show distributions of the $OD_{492}$ values in Table 3a and Table 3b, respectively, wherein the $OD_{492}$ values obtained from the ATLV-carrier were shown as a closed circle and the $OD_{492}$ values obtained from the normal human serum were shown as an open circle. Cutoff value was determined using the $OD_{492}$ values of the ten normal human serums and used for determination as to whether the specimens are positive or negative for the anti-ATLA antibody. The cutoff value was calculated by the equation: cutoff value = ((mean value of $OD_{492}$ values of the normal human serum) +2SD). When the presence of the anti-ATLA antibody in each serum specimen was assayed using this cutoff value, all ATLV-carrier serums were determined to be positive and all normal human serums were determined to be negative.

From the results shown in Tables 3a and 3b and FIGS. 4a and 4b, it can be seen that ELISA for the anti-ATLA antibody using the peptide prepared in Example 15 or the peptide prepared in Example 16 of the present invention suppresses the non-specific reaction and makes it possible to determine as to whether the specimen is positive or negative with high sensitivity.

TABLE 3a

| Normal human serum | | ATLV-carrier serum | | | |
|---|---|---|---|---|---|
| Serum No. | $OD_{492}$ | Serum No. | $OD_{492}$ | Serum No. | $OD_{492}$ |
| 1 | 0.167 | 1 | 2.549 | 11 | 2.335 |
| 2 | 0.187 | 2 | 2.598 | 12 | 2.583 |
| 3 | 0.228 | 3 | 2.356 | 13 | 2.591 |
| 4 | 0.159 | 4 | 2.442 | 14 | 2.435 |
| 5 | 0.169 | 5 | 2.670 | 15 | 2.568 |
| 6 | 0.110 | 6 | 2.626 | 16 | 2.123 |
| 7 | 0.119 | 7 | 2.354 | 17 | 2.397 |
| 8 | 0.057 | 8 | 2.444 | 18 | 2.687 |
| 9 | 0.093 | 9 | 2.521 | 19 | 2.488 |
| 10 | 0.124 | 10 | 2.241 | 20 | 2.626 |
| Mean | 0.134 | — | | | |
| SD | 0.024 | — | | | |
| Cutoff value | | 0.182 | | | |

TABLE 3b

| Normal human serum | | ATLV-carrier serum | | | |
|---|---|---|---|---|---|
| Serum No. | $OD_{492}$ | Serum No. | $OD_{492}$ | Serum No. | $OD_{492}$ |
| 1 | 0.153 | 1 | 2.187 | 11 | 2.581 |
| 2 | 0.126 | 2 | 2.545 | 12 | 2.564 |
| 3 | 0.172 | 3 | 2.536 | 13 | 2.664 |
| 4 | 0.148 | 4 | 2.365 | 14 | 2.346 |
| 5 | 0.154 | 5 | 2.714 | 15 | 2.593 |
| 6 | 0.168 | 6 | 2.669 | 16 | 2.555 |
| 7 | 0.111 | 7 | 2.263 | 17 | 2.323 |
| 8 | 0.108 | 8 | 2.121 | 18 | 2.492 |
| 9 | 0.100 | 9 | 2.376 | 19 | 2.537 |
| 10 | 0.168 | 10 | 2.458 | 20 | 2.641 |
| Mean | 0.141 | — | | | |
| SD | 0.027 | — | | | |
| Cutoff value | | 0.195 | | | |

EXAMPLE 23

Specimens

ATLV-carrier serum (22 specimens)
Normal human serum (2 specimens)

ELISA

Each serum specimen was assayed for the presence of the anti-ATLA antibody by the following ELISA in which an absorbance was measured.

The peptide prepared in Example 1 or the peptide prepared in Example 15 were each dissolved in 0.01M carbonate buffer (pH 9.5) to prepare a solution containing each peptide. In addition, a solution containing both peptides was prepared by mixing the above two peptide solutions at a ratio of 1:10 (the former solution:the latter solution). Each 100 μl of the resulting peptide solutions was added to a cup for ELISA made of polystyrene (the same as mentioned above) and the mixture was allowed to stand at 4° C. overnight so that the peptide is coated on the cup. After removing the peptide solution in the cups, to each cup was added PBS (200 μl) containing 20% by volume of normal goat serum and the mixture was allowed to stand at room temperature for 3 hours to block non-specific protein binding sites. The cups were then washed with PBS containing 0.05% by volume of Tween 20 (×3) and then with PBS (×1).

Using PBS containing 10% by volume of normal goat serum and 0.05% by volume of Tween 20 as a diluent, the diluent and each serum specimen (22 specimens of the ATLV-carrier serum and 2 specimens of the normal human serum) were mixed at a ratio of 20:1 (diluent:-specimen; v/v) and each 100 μl of the resulting diluted serum was then added to the above cup. After incubating at 37° C. for 1 hour, the cups were washed with PBS containing 0.05% by volume of Tween 20 (×3) and then with PBS (×1).

To each resulting assay cup was added PBS containing horseradish peroxidase conjugated goat anti-human IgG antibody (diluted at an optimal concentration with PBS containing 10% by volume of normal goat serum and 0.2% by volume of Tween 20; 100 μl). After incubation at 37° C. for 30 minutes, these cups were washed with PBS containing 0.05% by volume of Tween 20 (×3) and then with PBS (×1). To each resulting assay cup was added a substrate [o-phenylenediamine dissolved in 0.1M citrate/phosphate buffer containing 0.02% by volume of hydrogen peroxide (pH 5.6) at a concentration of 0.3% by weight; 100 μl]. After the mixtures were allowed to stand at room temperature for 15 minutes, to each mixture was added 1N sulfuric acid (100 μl) to stop the reaction and an absorbance at 492 nm ($OD_{492}$) of each reaction solution was measured.

Results

The results are shown in Table 4. Cutoff value was determined using the $OD_{492}$ values of the two normal human serums and used for determination as to whether the specimens are positive or negative for the anti-ATLA antibody. The cutoff value was calculated by the equation: cutoff value = ((mean value of $OD_{492}$ values of the normal human serum) +2SD). When the presence of the anti-ATLA antibody in each serum specimen was assayed using this cutoff value, all ATLV-carrier serums were determined to be positive.

From the results shown in Table 4, it was shown that the assay using the mixture of the peptide prepared in Example 1 and the peptide prepared in Example 15 gives higher absorbance than the assay using each single peptide when the presence of the anti-ATLA antibody is determined by measuring the absorbance in ELISA for those serum specimens showing relatively lower anti-ATLA antibody value, thereby avoiding for erroneously determining the specimen to be negative.

TABLE 4

| | Peptide | | | | | |
|---|---|---|---|---|---|---|
| | Peptide prepared in Ex. 1 | | Peptide prepared in Ex. 15 | | Mixture of peptides | |
| | Serum No. | $OD_{492}$ | Serum No. | $OD_{492}$ | Serum No. | $OD_{492}$ |
| ATLV- | 1 | 1.674 | 1 | 0.811 | 1 | 1.480 |

TABLE 4-continued

| | Peptide | | | | | |
|---|---|---|---|---|---|---|
| | Peptide prepared in Ex. 1 | | Peptide prepared in Ex. 15 | | Mixture of peptides | |
| | Serum No. | OD$_{492}$ | Serum No. | OD$_{492}$ | Serum No. | OD$_{492}$ |
| carrier serum | 2 | 1.328 | 2 | 0.635 | 2 | 1.046 |
| | 3 | 0.217 | 3 | 0.205 | 3 | 0.129 |
| | 4 | 0.371 | 4 | 0.325 | 4 | 0.230 |
| | 5 | 0.176 | 5 | 0.182 | 5 | 0.117 |
| | 6 | 0.170 | 6 | 0.183 | 6 | 0.104 |
| | 7 | 1.329 | 7 | 1.060 | 7 | 1.057 |
| | 8 | 1.314 | 8 | 1.042 | 8 | 1.028 |
| | 9 | 0.207 | 9 | 0.202 | 9 | 0.423 |
| | 10 | 0.143 | 10 | 0.100 | 10 | 0.228 |
| | 11 | 2.406 | 11 | 2.175 | 11 | 2.211 |
| | 12 | 0.747 | 12 | 0.522 | 12 | 0.750 |
| | 13 | 2.767 | 13 | 2.760 | 13 | 2.723 |
| | 14 | 0.111 | 14 | 0.101 | 14 | 0.180 |
| | 15 | 2.287 | 15 | 1.078 | 15 | 2.181 |
| | 16 | 0.480 | 16 | 0.510 | 16 | 0.401 |
| | 17 | 1.484 | 17 | 0.611 | 17 | 1.229 |
| | 18 | 0.258 | 18 | 0.194 | 18 | 0.293 |
| | 19 | 2.779 | 19 | 2.755 | 19 | 2.743 |
| | 20 | 1.231 | 20 | 1.107 | 20 | 1.161 |
| | 21 | 0.292 | 21 | 0.206 | 21 | 0.250 |
| | 22 | 1.818 | 22 | 1.505 | 22 | 1.680 |
| Normal human serum | 1 | 0.074 | 1 | 0.055 | 1 | 0.071 |
| | 2 | 0.062 | 2 | 0.049 | 2 | 0.059 |
| | Mean | 0.068 | Mean | 0.052 | Mean | 0.065 |
| | SD | 0.0085 | SD | 0.0042 | SD | 0.0085 |
| Cutoff value | 0.085 | | 0.060 | | 0.082 | |

EXAMPLE 24

Specimens

ATLV-carrier serum (15 specimens)
Normal human serum (15 specimens)

ELISA

Each serum specimen was assayed for the presence of the anti-ATLA antibody by the following ELISA in which an absorbance was measured.

The peptide prepared in Example 1 or the peptide prepared in Reference Example 9 were each dissolved in 0.01M carbonate buffer (pH 9.5) to prepare a solution containing each peptide. In addition, a solution containing both peptides was prepared by mixing the above two solutions at a concentration ratio of 1:1 (the former:the latter). Each 100 μl of the resulting peptide solutions was added to a cup for ELISA made of polystyrene (the same as mentioned above) and the mixture was allowed to stand at 4° C. overnight so that the peptide is coated on the cup. After removing the peptide solution in these cups, to each cup was added PBS (200 μl) containing 20% by volume of normal goat serum and the mixture was allowed to stand at room temperature for 3 hours to block non-specific protein binding sites. After removing the blocking solution in the cups, the cups were dried and stored at 4° C.

Using PBS containing 10% by volume of normal goat serum and 0.05% by volume of Tween 20 as a diluent, the diluent and each serum specimen (15 specimens of the ATLV-carrier serum and 15 specimens of the normal human serum) was mixed at a ratio of 20:1 (diluent:specimen; v/v) and each 100 μl of the resulting diluted serums was added to above each assay cup. After incubation at 37° C. for 1 hour, the cups were washed with PBS containing 0.05% by volume of Tween 20 (×3) and then with PBS (×1).

To each resulting assay cup was added PBS containing horseradish peroxidase conjugated goat anti-human IgG antibody (diluted at an optimal concentration with PBS containing 10% by volume of normal goat serum and 0.2% by volume of Tween 20; 100 μl). After incubation at 37° C. for 30 minutes, these cups were washed with PBS containing 0.05% by volume of Tween 20 (×3) and then with PBS (×1). To each resulting assay cup was added a substrate [o-phenylenediamine dissolved in 0.1M citrate/phosphate buffer containing 0.02% by volume of hydrogen peroxide (pH 5.6) at a concentration of 0.3% by weight; 100 μl]. After the mixtures were allowed to stand at room temperature for 15 minutes, to each mixture was added 1N sulfuric acid (100 μl) to stop the reaction and an absorbance at 492 nm (OD$_{492}$) of each reaction solution was measured.

Results

The results are shown in Table 5. Cutoff value was determined using the OD$_{492}$ values of the fifteen normal human serums and used for determination as to whether the specimens are positive or negative for the anti-ATLA antibody. The cutoff value was calculated by the equation: cutoff value = ((mean value of OD$_{492}$ values of the normal human serum) +2SD). When the presence of the anti-ATLA antibody in each serum specimen was assayed using this cutoff value, all ATLV-carrier serums were determined to be positive and all normal human serums were determined to be negative.

From the results shown in Table 5, those specimens which were determined to be negative in ELISA using one of the peptides prepared in Example 1 and Example 9 but were determined to be positive in ELISA using the other peptide were found to be determined positive in ELISA using the mixture of these two peptides with high sensitivity.

TABLE 5

| | Peptide | | | | | |
|---|---|---|---|---|---|---|
| | Peptide prepared in Ex. 1 | | Peptide prepared in Ex. 9 | | Mixture of peptides | |
| | Serum No. | OD$_{492}$ | Serum No. | OD$_{492}$ | Serum No. | OD$_{492}$ |
| ATLV-carrier serum | 1 | 2.926 | 1 | 0.873 | 1 | 2.015 |
| | 2 | 1.732 | 2 | 0.973 | 2 | 1.554 |
| | 3 | 2.957 | 3 | 1.405 | 3 | 2.345 |
| | 4 | 0.576 | 4 | 0.099 | 4 | 0.465 |
| | 5 | 2.853 | 5 | 1.623 | 5 | 2.239 |
| | 6 | 2.688 | 6 | 1.437 | 6 | 2.065 |
| | 7 | 2.156 | 7 | 0.137 | 7 | 1.785 |
| | 8 | 2.535 | 8 | 0.088 | 8 | 2.102 |
| | 9 | 1.036 | 9 | 0.111 | 9 | 0.859 |
| | 10 | 0.182 | 10 | 1.029 | 10 | 0.895 |
| | 11 | 0.703 | 11 | 1.071 | 11 | 0.954 |
| | 12 | 0.861 | 12 | 1.156 | 12 | 0.996 |
| | 13 | 2.796 | 13 | 1.061 | 13 | 1.967 |
| | 14 | 2.274 | 14 | 0.549 | 14 | 1.745 |
| | 15 | 2.015 | 15 | 1.478 | 15 | 1.532 |
| Normal human serum | 1 | 0.035 | 1 | 0.078 | 1 | 0.055 |
| | 2 | 0.174 | 2 | 0.062 | 2 | 0.086 |
| | 3 | 0.151 | 3 | 0.040 | 3 | 0.068 |
| | 4 | 0.093 | 4 | 0.089 | 4 | 0.080 |
| | 5 | 0.089 | 5 | 0.133 | 5 | 0.085 |
| | 6 | 0.114 | 6 | 0.103 | 6 | 0.100 |
| | 7 | 0.133 | 7 | 0.099 | 7 | 0.102 |
| | 8 | 0.104 | 8 | 0.083 | 8 | 0.095 |
| | 9 | 0.111 | 9 | 0.151 | 9 | 0.110 |
| | 10 | 0.070 | 10 | 0.065 | 10 | 0.071 |
| | 11 | 0.125 | 11 | 0.093 | 11 | 0.093 |
| | 12 | 0.145 | 12 | 0.097 | 12 | 0.099 |
| | 13 | 0.078 | 13 | 0.100 | 13 | 0.087 |
| | 14 | 0.088 | 14 | 0.094 | 14 | 0.092 |
| | 15 | 0.127 | 15 | 0.154 | 15 | 0.131 |

TABLE 5-continued

| | Peptide | | | | | |
|---|---|---|---|---|---|---|
| | Peptide prepared in Ex. 1 | | Peptide prepared in Ex. 9 | | Mixture of peptides | |
| | Serum No. | OD$_{492}$ | Serum No. | OD$_{492}$ | Serum No. | OD$_{492}$ |
| | Mean | 0.109 | Mean | 0.096 | Mean | 0.092 |
| | SD | 0.0351 | SD | 0.0312 | SD | 0.0220 |
| Cutoff value | 0.180 | | 0.158 | | 0.136 | |

EXAMPLE 25

To a solution (10 ml) of agarose particles (Cepharose 4B manufactured by Pharmacia) activated with cyanogen bromide and buffered with 0.1M Tris-HCl buffer (pH 7.4) was added the peptide (100 mg) prepared in Example 1 and the mixture was stirred at 4° C. overnight to proceed the reaction to give an adsorbent (about 10 ml) where the peptide prepared in Example 1 was immobilized.

EXAMPLE 26

To a solution (10 ml) of agarose particles (the same as mentioned above) activated with cyanogen bromide and buffered with 0.1M Tris-HCl buffer (pH 7.4) was added the peptide (100 mg) prepared in Example 15 and the mixture was stirred at 4° C. overnight to proceed the reaction to give an adsorbent (about 10 ml) where the peptide prepared in Example 15 was immobilized.

EXAMPLE 27

To a solution (10 ml) of agarose particles (the same as mentioned above) activated with cyanogen bromide and buffered with 0.1M Tris-HCl buffer (pH 7.4) was added the peptide (100 mg) prepared in Example 16 and the mixture was stirred at 4° C. overnight to proceed the reaction to give an adsorbent (about 10 ml) where the peptide prepared in Example 16 was immobilized.

EXAMPLE 28

Cellulose particles (CM Cellulofine CL, available from Seikagaku Kogyo K. K.; 10 g) were suspended in anhydrous dioxane (prepared by distilling commercially available dioxane in the presence of metallic sodium; 50 ml). To the obtained suspension were added N-hydroxysuccinimide (0.5 g) and dicyclohexylcarbodiimide (1.0 g) and the mixture was stirred at room temperature overnight. The resulting particles were mixed with 0.02M phosphate buffer (pH 7.4) (20 ml) containing the peptide (20 mg) prepared in Example 1 and the mixture was stirred at 4° C. overnight. The obtained mixture was filtered by suction. The filtrate was subjected to analytical reversed phase high performance chromatography (the same as mentioned above), with which no further unreacted peptide was found (immobilization ratio of the peptide on the carrier: about 100%). Thus, there was prepared an adsorbent (about 10 g) in which the peptide (20 mg) prepared in Example 1 was immobilized.

EXAMPLES 29 to 39

Using each 20 mg of the peptides prepared in Examples 4 to 14, the procedure of Example 28 was repeated to give each about 10 g of adsorbents in which each 20 mg of these peptides was immobilized, respectively (immobilization ratio of each peptide on the carrier: about 100%).

EXAMPLE 40

The procedure of Example 28 was repeated except that polyvinyl alcohol particles (TSK-gel CM-Toyo Parl 650C manufactured by Toso K. K.; 10 g) were used in place of the cellulose particles (10 g) to give about 10 mg of polyvinyl alcohol particles in which 20 mg of the peptide prepared in Example 1 was immobilized (immobilization ratio of the peptide on the carrier: about 93%).

EXAMPLES 41 to 51

Using each 20 mg of the peptides prepared in Examples 4 to 14, the procedure of Example 40 was repeated to give each about 10 g of adsorbents in which each 20 mg of these peptides was immobilized. Table 6 shows each immobilization ratio of the obtained adsorbents on the carrier.

TABLE 6

| Example | Example which shows synthesis of the peptide used for immobilization | Immobilization ratio (%) |
|---|---|---|
| 41 | 4 | 93 |
| 42 | 5 | 95 |
| 43 | 6 | 90 |
| 44 | 7 | 93 |
| 45 | 8 | 94 |
| 46 | 9 | 94 |
| 47 | 10 | 93 |
| 48 | 11 | 95 |
| 49 | 12 | 91 |
| 50 | 13 | 94 |
| 51 | 14 | 90 |

EXAMPLE 52

Porous glass particles (CPG-10-1000 manufactured by Electro-Nucleonics, USA; 10 g) were refluxed in a toluene solution (100 ml) containing γ-aminopropyltriethoxysilane (5 ml) for 24 hours. The obtained mixture was washed with anhydrous dioxane and filtrated by suction. The resulting particles were suspended in anhydrous dioxane (100 ml) and to the suspension was added anhydrous succinic acid (3 g) and the mixture was stirred at room temperature overnight. The mixture was washed with anhydrous dioxane and filtered by suction. The resulting particles were suspended in anhydrous dioxane (50 ml) and to the suspension were added N-hydroxysuccinic acid imide (0.5 g) and dicyclohexylcarbodiimide (1.0 g) and the mixture was stirred at room temperature overnight. The resulting mixture was washed with 0.02M phosphate buffer [pH 7.4] and filtered by suction. The resulting particles were mixed with 0.02M phosphate buffer (pH 7.4) (20 ml) containing the peptide (20 mg) prepared in Example 1 and the mixture was stirred at 4° C. overnight. The resulting mixture was filtered by suction to give about 10 g of an adsorbent in which 20 mg of the peptide prepared in Example 1 was immobilized (immobilization ratio: about 100%).

EXAMPLE 53

Using the peptide (20 mg) prepared in Example 15, the procedure of Example 52 was repeated to give about 10 g of an adsorbent in which 20 mg of the peptide was immobilized (immobilization ratio: about 100%).

EXPERIMENT 1

The adsorbent prepared in Example 25 was filled in a column (manufactured by Amicon; 10 mm φ×150 mm) to prepare a column for affinity chromatography. The column was washed with 0.1M Tris-HCl buffer (pH 8.5) containing 0.15M sodium chloride and then with 0.5M Tris-HCl buffer and equilibrated with 0.1M Tris-HCl buffer. An anti-ATLA antibody positive serum (10 ml) was dialyzed against 0.1M Tris-HCl buffer overnight and passed through the equilibrated column. After washing the column with 0.1M Tris-HCl buffer, the anti-ATLA antibody bound to the peptide immobilized onto Cepharose 4B was eluted with 0.5M Tris-HCl buffer. The presence of the anti-ATLA antibody was assayed for each fraction using the procedure as in Example 21. Nearly 100% of the serum anti-ATLA antibody was detected in the eluted fraction but the anti-ATLA antibody could not detected in the passed through fraction.

EXPERIMENT 2

The adsorbent prepared in Example 26 was filled in a column (the same as mentioned above) in the same manner as in Experiment 1 to prepare a column for affinity chromatography. An anti-ATLA antibody positive serum (10 ml) was dialyzed against 0.1M Tris-HCl buffer overnight and passed through the column. The serum anti-ATLA antibody was collected and the presence of the anti-ATLA antibody was assayed for each fraction using the procedure as in Example 21. Nearly 100% of the serum anti-ATLA antibody was detected in the eluted fraction but the anti-ATLA antibody could not be detected in the passed through fraction.

EXPERIMENT 3

The adsorbent prepared in Example 27 was filled in a column (the same as mentioned above) in the same manner as in Experiment 1 to prepare a column for affinity chromatography. An anti-ATLA antibody positive serum (10 ml) was dialyzed against 0.1M Tris-HCl buffer overnight and passed through the column. The serum anti-ATLA antibody was collected and the presence of the anti-ATLA antibody was assayed for each fraction using the procedure as in Example 21. Nearly 100% of the serum anti-ATLA antibody was detected in the eluted fraction but the anti-ATLA antibody could not be detected in the passed through fraction.

EXPERIMENT 4

An anti-ATLA antibody positive serum (10 ml) was dialyzed against 0.01M phosphate buffer (pH 7.2) containing 0.15M sodium chloride at 4° C. overnight. To this serum (1 ml) was added the adsorbent (1 ml) prepared in Example 28 and the mixture was shaked at 37° C. for 1 hour and then washed with the above phosphate buffer (30 ml). An amount of the anti-ATLA antibody in the serum after dialysis and that in a washing solution were determined in the same manner as in Example 21 by measuring each $OD_{492}$, from which a ratio of the anti-ATLA antibody adsorbed by the adsorbent was calculated. As a result, it was found that about 100% of the serum anti-ATLA antibody was adsorbed by the adsorbent.

EXPERIMENTS 5 to 9

Using the adsorbents prepared in Examples 29 to 33, the procedure of Experiment 4 was repeated to conduct experiment as to the adsorption of the anti-ATLA antibody in the serum. An amount of the anti-ATLA antibody in the serum after dialysis and that in a washing solution were determined in the same manner as in Example 21 by measuring each $OD_{492}$, from which a ratio of the anti-ATLA antibody adsorbed by the adsorbent was calculated. As a result, it was found that about 100% of the anti-ATLA antibody in the serum was adsorbed by the adsorbent.

EXPERIMENT 10

After dialyzing an anti-ATLA antibody positive serum (10 ml) in the same manner as in Experiment 4, the adsorbent prepared in Example 40 was added to the serum and experiment was conducted as to adsorption of the anti-ATLA antibody in the serum. As a result, it was found that about 100% of the anti-ATLA antibody in the serum was adsorbed by the adsorbent.

EXPERIMENT 11

After dialyzing an anti-ATLA antibody positive serum (10 ml) in the same manner as in Experiment 4, the adsorbent prepared in Example 38 was added to the serum and experiment was conducted as to adsorption of the anti-ATLA antibody in the serum. As a result, it was found that about 100% of the anti-ATLA antibody in the serum was adsorbed by the adsorbent.

---

What is claimed is:

1. A peptide of the general formula:

H-X-A-Y wherein A is a peptide fragment comprising 6 to 50 amino acids, X is a peptide fragment comprising 1 to 10 Lys, and Y is hydroxy or amino group, said peptide being capable of specifically binding to an antibody having a specificity against an adult T cell leukemia associated antigen, A being selected from the group consisting of:

(a) -Pro-Pro-Pro-Pro-Ser-Ser-Pro-Thr-His-Asp-Pro-Pro-Asp-Ser-Asp-Pro-Gln-Ile-Pro-Pro-Tyr-Val-Glu-Pro-Thr-Ala-Pro-Gln-Val-Leu- (SEQ ID NO: 1), (b) -Pro-Pro-Pro-Pro-Ser-Ser-Pro-Thr-His-Asp-Pro-Pro-Asp-Ser-Asp-Pro-Gln-Ile-Pro- (SEQ ID NO: 28), (c) -Pro-Tyr-Val-Glu-Pro-Thr-Ala-Pro-Gln-Val-Leu- (SEQ ID NO: 29), (d) -Pro-Val-Met-His-Pro-His-Gly-Ala-Pro-Pro-Asn-His-Arg-Pro-Trp-Gln-Met-Lys-Asp-Leu-Gln-Ala-Ile-Lys-Gln-Glu-Val-Ser-Gln-Ala-(SEQ ID NO: 30), (e) -Gly-Leu-Pro-Glu-Gly-Thr-Pro-Lys-Asp-Pro-Ile-Leu-Arg-Ser-Leu-Ala-Tyr-Ser-Asn-Ala-Asn-Lys-Glu-Cys-Gln-Lys-Leu-Leu-Gln-Ala-(SEQ ID NO: 31), (f) -Asp-Pro-Ile-Leu-Arg-Ser-Leu-Ala-Tyr-Ser-Asn-Ala-Asn-Lys-Glu-Cys-Gln-Lys-Leu- (SEQ ID NO: 32), (g) -Gly-Asp-Tyr-Ser-Pro-Ser-Cys-Cys-Thr-Leu-Thr-Ile-Gly-Val-Ser-Ser-Tyr-His-Ser-Lys-Pro-Cys-Asn-Pro-Ala-Gln-Pro-Val-Cys-Ser-(SEQ ID NO: 33), (h) -Thr-Lys-Lys-Pro-Asn-Arg-Asn-Gly-Gly-Gly-Tyr-Tyr-Ser-Ala-Ser-Tyr-Ser-Asp-Pro-Cys-Ser-Leu-Lys-Cys-Pro-Tyr-Leu- (SEQ ID NO: 34), (i) -Phe-Leu-Asn-Thr-Glu-Pro-Ser-Gln-Leu-Pro-Pro-Thr-Ala-Pro-Pro-Leu-Leu-Pro-His-Ser-Asn-Leu-Asp-His-Ile- (SEQ ID NO: 3), (j) -Thr-Pro-Leu-Leu-Tyr-Pro-Ser-Leu-Ala-Leu-Pro-Ala-Pro-His-Leu-Thr-Leu-Pro-Phe-Asn-Trp-Thr-His-Cys-Phe-Asp-Pro-Gln-Ile-Gln-(SEQ ID NO: 35), (k) -Thr-Pro-Cys-His-Asn-Ser-Leu-Ile-Leu-Pro-Pro-Phe-Ser-Leu-Ser-Pro-Val-Pro-Thr-Leu-Gly-Ser-Arg-Arg-Ala-Val-Pro-Val-Ala- (SEQ ID NO: 36), (l) -Val-Asp-Lys-Asp-Ile-Ser-Gln-Leu-Thr-Gln-Ala-Ile-Val-Lys-Asn-His-Lys-Asn-Leu-Leu-Lys-Ile-Ala-Gln-Tyr-Ala-Ala-Gln-Asn-Arg-Arg-Gly-Leu-Asp-Leu-Leu-Phe- (SEQ ID NO: 37), (m) -Cys-Arg-Phe-Pro-Asn-Ile-Thr-Asn-Ser-His-Val-Pro-Ile-Leu-Gln-Glu-Arg-Pro-Pro-Leu-Glu-Asn-Arg-Val-Leu-Thr-Gly-Trp-Gly-Leu- (SEQ ID NO: 38), (n) -Leu-Ala-Gly-Pro-Cys-Ile-Leu-Arg-Gln-Leu-Arg-His-Leu-Pro-Ser-Arg-Val-Arg-Tyr-Pro-His-Tyr-Ser-Leu-Ile-Lys-Pro-Glu-Ser-Ser-Leu- (SEQ ID NO: 39), (o) -Tyr-Ala-Ala-Gln-Asn-Arg-Arg-Gly-Leu-Asp-Leu-Leu-Phe-Trp-Glu-Gln-Gly-Gly-Leu- (SEQ ID NO: 2), and (p) -Leu-Leu-Pro-His-Ser-Asn-Leu-Asp-His-Ile-Leu-Glu-Pro-Ser-Ile-Pro-Trp-Lys-Ser-Lys- (SEQ ID NO: 40), 2. The peptide according to claim 1 wherein A is a peptide fragment of the following amino acid sequence (SEQ ID NO: 1):

—Pro—Pro—Pro—Pro—Ser—Ser—Pro—Thr—His—Asp—Pro—Pro—Asp—Ser—Asp—Pro—Gln—Ile—Pro—Pro—Pro—Tyr—Val—Glu—Pro—Thr—Ala—Pro—Gln—Val—Leu—.

3. The peptide according to claim 1 wherein A is a peptide fragment of the following amino acid sequence (SEQ ID NO: 2):

—Tyr—Ala—Ala—Gln—Asn—Arg—Arg—Gly—Leu—Asp—Leu—Leu—Phe—Trp—Glu—Gln—Gly—Gly—Leu—.

4. The peptide according to claim 1 wherein A is a peptie fragment of the following amino acid sequence (SEQ ID NO: 3):

—Phe—Leu—Asn—Thr—Glu—Pro—Ser—Gln—Leu—Pro—Pro—Thr—Ala—Pro—Pro—Leu—Leu—Pro—His—Ser—Asn—Leu—Asp—His—Ile—.

* * * * *

UNITED STATES PATENT AND TRADEMARK OFFICE
CERTIFICATE OF CORRECTION

PATENT NO. : 5,194,586
DATED : March 16, 1993
INVENTOR(S) : YOSHIAKI MAEDA ET AL It is certified that error appears in the above-identified patent and that said Letters Patent is hereby corrected as shown below:

Claim 1 (column 51, lines 9-11), delete " (k) -Thr-Pro-Cys-His-Asn-Ser-Leu-Ile-Leu-Pro-Pro-Phe-Ser-Leu-Ser-Pro-Val-Pro-Thr-Leu-Gly-Ser-Arg-Arg-Ala-Val-Pro-Val-Ala-(SEQ ID NO: 36)," and insert -- (k) -Thr-Pro-Cys-His-Asn-Ser-Leu-Ile-Leu-Pro-Pro-Phe-Ser-Leu-Ser-Pro-Val-Pro-Thr-Leu-Gly-Ser-Arg-Ser-Arg-Arg-Ala-Val-Pro-Val-Ala- (SEQ ID NO:36),--.

Claim 4 (column 52, line 21), delete "peptie", and insert --peptide--.

Signed and Sealed this

Seventh Day of December, 1993

Attest:

BRUCE LEHMAN

*Attesting Officer*      *Commissioner of Patents and Trademarks*